(12) United States Patent
Roche et al.

(10) Patent No.: US 8,888,855 B2
(45) Date of Patent: Nov. 18, 2014

(54) REVERSE SHOULDER HUMERAL ADAPTER TRAYS

(71) Applicant: Exactech, Inc., Gainesville, FL (US)

(72) Inventors: Christopher Roche, Gainesville, FL (US); Matthew Hamilton, Gainesville, FL (US); Phong Diep, Gainesville, FL (US)

(73) Assignee: Exactech, Inc., Gainesville, FL (US)

( * ) Notice: Subject to any disclaimer, the term of this patent is extended or adjusted under 35 U.S.C. 154(b) by 51 days.

(21) Appl. No.: 13/905,599

(22) Filed: May 30, 2013

(65) Prior Publication Data

US 2013/0325131 A1 Dec. 5, 2013

Related U.S. Application Data

(60) Provisional application No. 61/653,860, filed on May 31, 2012, provisional application No. 61/779,363, filed on Mar. 13, 2013.

(51) Int. Cl.
*A61F 2/40* (2006.01)
*A61F 2/30* (2006.01)

(52) U.S. Cl.
CPC .................. *A61F 2/40* (2013.01); *A61F 2/4014* (2013.01); *A61F 2002/30331* (2013.01); *A61F 2002/30367* (2013.01); *A61F 2002/30433* (2013.01); *A61F 2002/305* (2013.01); *A61F 2002/30553* (2013.01); *A61F 2002/30616* (2013.01); *A61F 2002/4022* (2013.01)
USPC ................... 623/19.11; 623/19.12; 623/19.13

(58) Field of Classification Search
CPC ...... A61F 2/40; A61F 2/38; A61F 2002/4062
USPC ......................... 623/19.11–19.14, 22.11–22.4
See application file for complete search history.

(56) References Cited

U.S. PATENT DOCUMENTS

| | | | |
|---|---|---|---|
| 7,011,686 B2 | 3/2006 | Ball | |
| 7,175,663 B1 | 2/2007 | Stone | |
| 7,241,314 B1 | 7/2007 | Winslow | |
| 2007/0244563 A1 | 10/2007 | Roche et al. | |
| 2009/0171462 A1 | 7/2009 | Poncet | |
| 2009/0216332 A1 | 8/2009 | Splieth et al. | |
| 2010/0087927 A1 | 4/2010 | Roche et al. | |
| 2011/0060417 A1 | 3/2011 | Simmen | |

OTHER PUBLICATIONS

International Search Report and The Written Opinion Dated Aug. 30, 2013 from the International Searching Authority Re: Application No. PCT/US13/43321.

(Continued)

*Primary Examiner* — Jason-Dennis Stewart
(74) *Attorney, Agent, or Firm* — Greenberg Traurig, LLP

(57) ABSTRACT

Disclosed herein are components of a reverse shoulder prosthesis. In an embodiment, a reverse shoulder prosthesis includes a humeral adapter tray configured to sit near a resected surface of a humerus, the humeral adapter tray comprising: a cavity; a central bore; and a distal face including a boss, the boss: (i) configured as an extension of the distal face, (ii) posteriorly offset from the central bore by at least 10 mm, and (iii) configured to engage a humeral stem; and a humeral liner comprising: a distal rim configured to sit within the cavity of the humeral adapter tray; and a concave articulating surface configured to mate with a convex articulating surface of a glenosphere. In an embodiment, the boss, in addition to being posteriorly offset, is superiorly offset from the central bore by at least 8 mm. In an embodiment, the reverse shoulder a humeral stem which engages the boss.

20 Claims, 22 Drawing Sheets

(56) References Cited

OTHER PUBLICATIONS

Gutierrez, S. et al. Evaluation of abduction range of motion and avoidance of inferior scapular impingement in a reverse shoulder model in Journal of Shoulder and Elbow Surgery, vol. 17; Issue 4, pp. 608-615, Mar. 6, 2008.
De Wilde, L.F., et al. Shoulder Prostheses Treating Cuff Tear Arthropathy: A Comparative Biomechanical Study, JOR, vol. 22, pp. 1222-1230, 2004.
Lemieux, P.O., et al. Influence of the Medial Offset of the Proximal Humerus on the Glenohumeral Destabilizing Forces During Arm Elevation: A Numerical Sensitivity Study, Computer Methods in Biomechanics and Biomedical Engineering, In Press, 2012.
Flatow, EL, et al. A History of Reverse Total Shoulder Arthroplasty, CORR, vol. 469, pp. 2432-2439, Jan. 7, 2011.
Redfern, TR., Wallace, WA., History of Shoulder Replacement Surgery, In: Wallace, WA., ed., Joint Replacement in the Shoulder and Elbow, Oxford, UK: Butterworth and Heinemann; 1998, pp. 6-16.
Reeves, B., Jobbins, B., Dowson, D., Wright, VA., A Total Shoulder Endoprosthesis, Eng. Med. 1974; vol. 1, No. 3, pp. 64-67.
Brostrom, L., et al., The Kessel Prosthesis in Total Shoulder Arthroplasty, CORR. No. 277, pp. 155-160, Apr. 1992.
Wretenberg, P., et al. The Kessel Total Shoulder Athroplasty: a 13 to 16 Year Retrospective Follow-up. CORR No. 365, pp. 100-103, Aug. 1999.
Grammont, PM., et al. Etude et Realisation D'une Novelle Prosthese D'Paule, Rhumatologie, vol. 39, No. 10, pp. 407-418, 1987.
Boileau, P., et al. Grammont Reverse Prosthesis: Design, Rationale, and Biomechanics, JSES, vol. 1S, pp. 147S-161S. Jan./Feb. 2005.
Nyffeler, RW, et al. Biomechanical Relevance of Glenoid Component Positioning in the Reverse Delta III Total Shoulder Prosthesis, JSES, vol. 14. No. 5, pp. 524-528, Sep./Oct. 2005.
Kontaxis, A. et al., The Biomechanics of Reverse Anatomy Shoulder Replacement—A Modeling Study., Clinical Biomechanics, vol. 24, pp. 254-260, Mar. 2009.
Ackland, DC., et al, Moment Arms of the Shoulder Musculature After Reverse Total Shoulder Arthroplasty, JBJS, vol. 92-A, No. 5, pp. 1221-1230, May 2010.

Frankle, M., et al. The Reverse Shoulder Prosthesis for Glenohumeral Arthritis Associated With Severe Rotator Cuff Deficiency. A Minimum Two-Year Follow-up Study of Sixty Patients, JBJS, vol. 87 A, No. 8, pp. 1697-1705, Aug. 2005.
Henninger, HB., et al., Effect of Lateral Offset Center of Rotation in Reverse Total Shoulder Arthroplasty: A Biomechanical Study, JSES, In Press, vol. 21, pp. 1128-1135, Sep. 2012.
Boileau, P., et al. Reverse Shoulder Arthroplasty Combined With a Modified Latissimus Dorsi and Teres Major Tendon Transfer for Shoulder Pseudoparalysis Associated With Dropping Arm, CORR. vol. 466, pp. 584-593, Jan. 25, 2008.
Boileau, P., et al. Reversed Shoulder Arthroplasty Combined With Modified L-Episcopo for Combined Loss of Active Elevation and External Rotation, JSES, vol. 19, pp. 20-30, Mar. 2010.
Favre, P. et al., Latissimus Dorsi Transfer to Restore External Rotation With Reverse Shoulder Arthroplasty: A Biomechanical Study, JSES. vol. 17, No. 4, pp. 650-658, Jul. 2008.
Roche, C., et al. Geometric Analysis of the Grammont Reverse Shoulder Prosthesis: An Evaluation of the Relationship Between Prosthetic Design Parameters and Clinical Failure Modes. Proceedings of the 2006 USA ISTA Meeting, 2006.
Roche, C., et al. An Evaluation of the Relationship Between Reverse Shoulder Design Parameters and Clinical Failure Modes, JSES, vol. 18, pp. 734-741, Sep. 2009.
Bergmann, G., et al. In Vivo Glenohumeral Contact Forces—Measurements in the First Patient 7 Months Preoperatively, Journal of Biomechanics. vol. 40, No. 10, pp. 2139-2149, 2007.
Onstott, E., et al., Consequences of Concomitant Subscapularis Repair With Reverse Total Shoulder Arthroplasty. Trans. of the 58th Annual ORS Meeting, 2012.
Gerber, C., et al., Latissimus Dorsi Transfer for the Treatment of Irreparable Rotator Cuff Tears, JBJS. vol. 88-A, No. 1, pp. 113-120, Jan. 2006.
Gerber, C. Single-stage Bilateral Total Shoulder Arthroplasty, JBJS, vol. 88-B, No. 6, Jun. 2006.
A report by Philipp Kropf, EPOCA Custom Offset Shoulder Prosthesis System, A report by Philipp Kropf, Business Briefing: Global Surgery 2003, pp. 1-2.
Dedy, NJ, Hurschler, C., Marquardt, B., Steinbeck, J., Effect of Posterior Offset Humeral Components o Range of Motion in Reverse Shoulder Arthroplasty, International Orthopaedics (SICOT) (Jun. 20, 2010) 35, pp. 549-554.

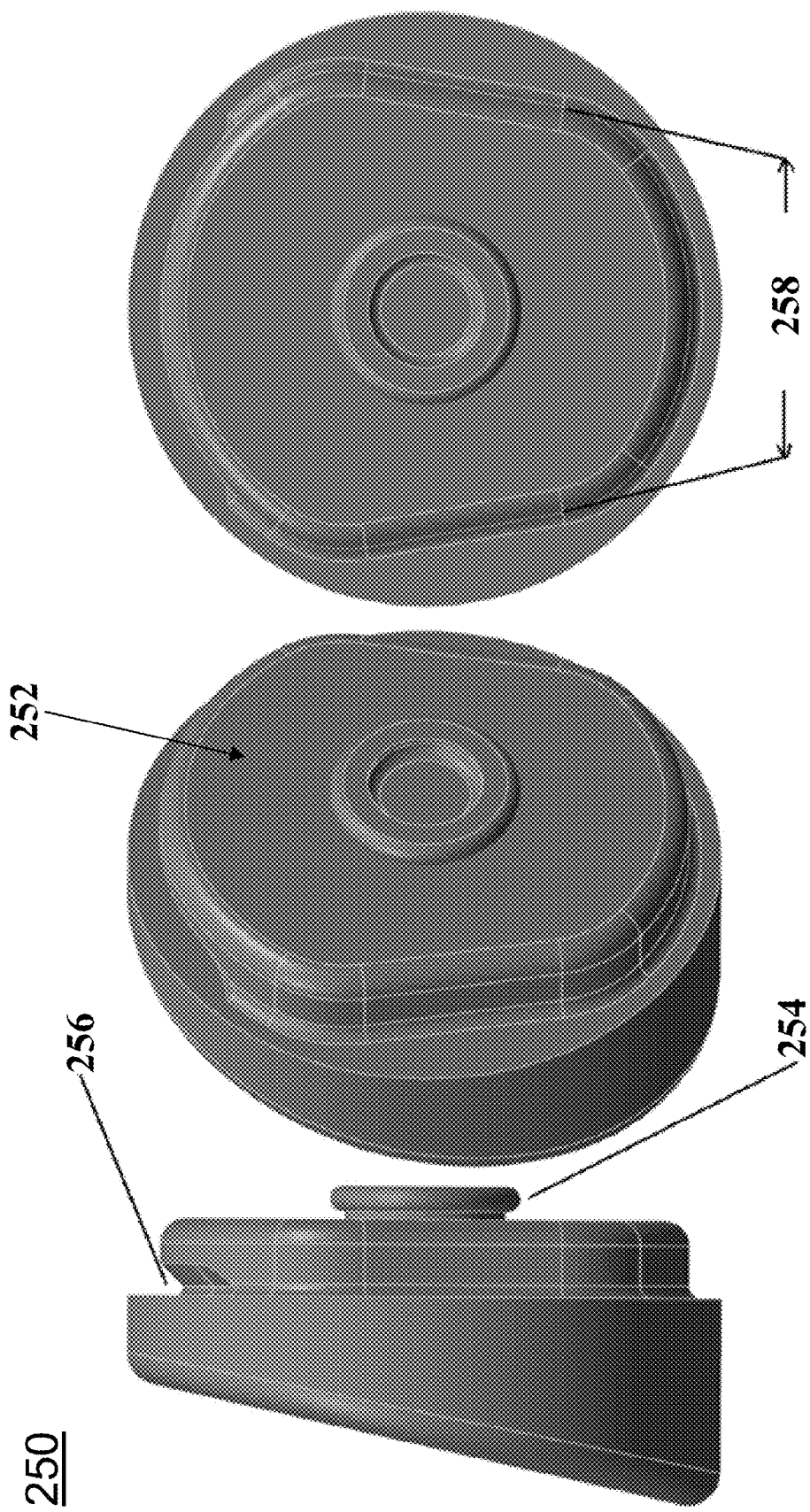

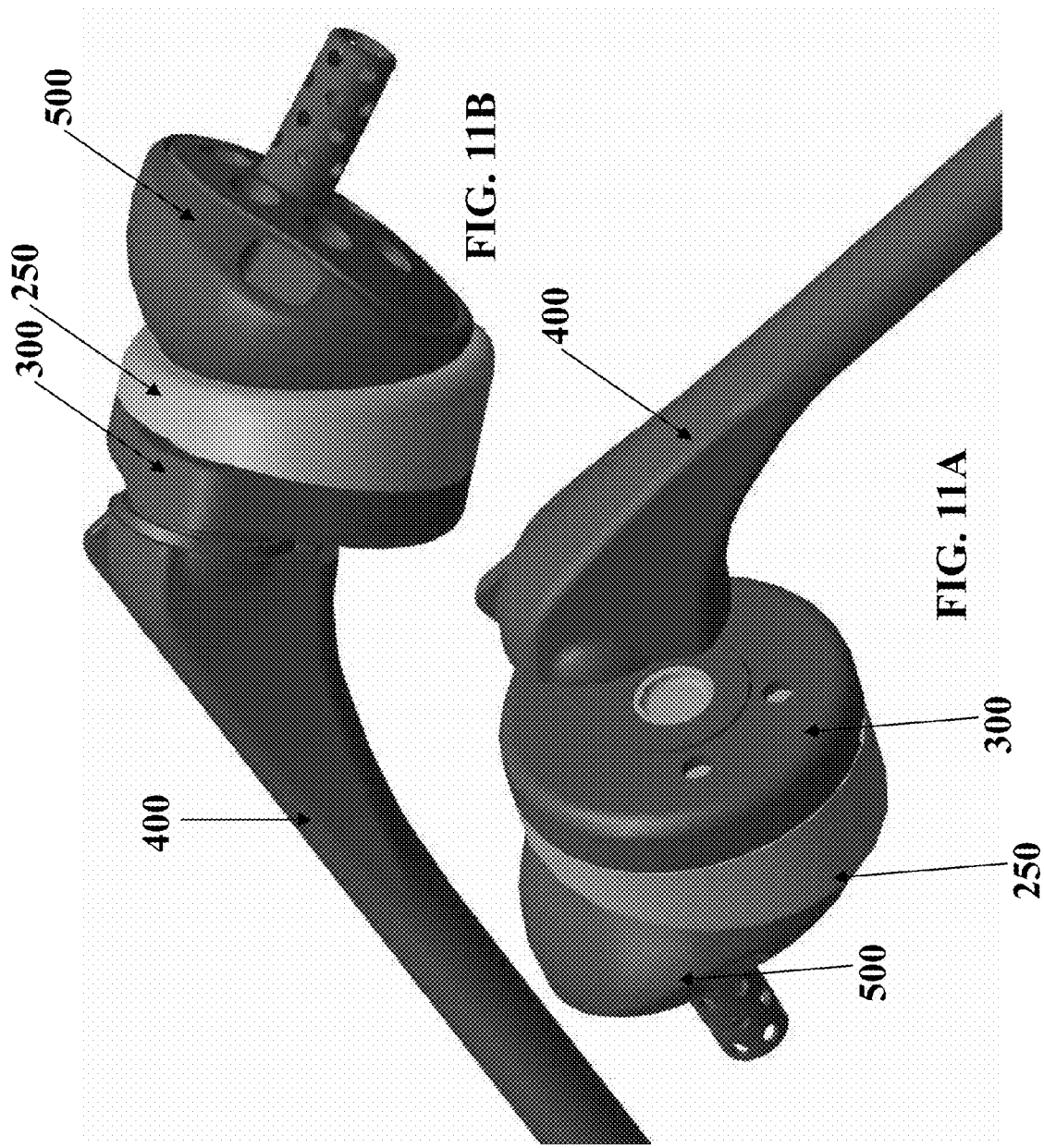

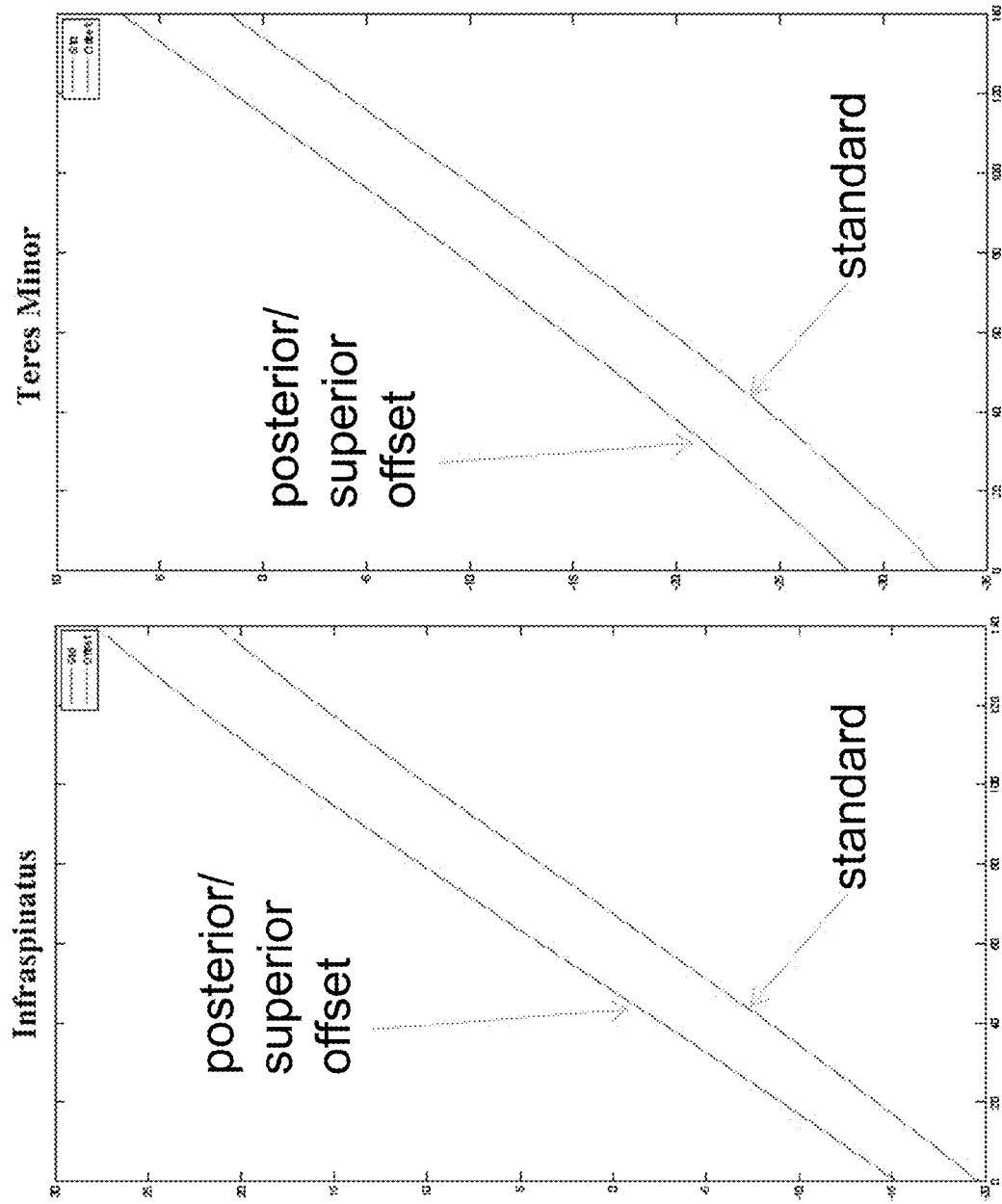

REVERSE SHOULDER HUMERAL ADAPTER TRAYS

RELATED APPLICATIONS

This application claims the benefit of U.S. Provisional Application Ser. No. 61/653,860, filed May 31, 2012 and U.S. Provisional Application Ser. No. 61/779,363, filed Mar. 13, 2013, and the entirety of these applications are hereby incorporated herein by reference for the teachings therein.

BACKGROUND

The reverse shoulder was first conceived in the early 1970's to treat patients suffering from rotator cuff tear arthropathy (CTA). The reverse shoulder inverts the anatomic concavities making the glenoid articular component convex and the humeral articular component concave, creating a fixed fulcrum that prevents the humerus from migrating superiorly.

SUMMARY

According to aspects illustrated herein, there is disclosed a reverse shoulder prosthesis that includes a humeral adapter tray configured to sit near a resected surface of a humerus, the humeral adapter tray comprising: a cavity; a central bore; and a distal face including a boss, the boss: (i) configured as an extension of the distal face, (ii) posteriorly offset from the central bore by at least 10 mm, and (iii) configured to engage a humeral stem; and a humeral liner comprising: a distal rim configured to sit within the cavity of the humeral adapter tray; and a concave articulating surface configured to mate with a convex articulating surface of a glenosphere. In an embodiment, the boss, in addition to being posteriorly offset, is superiorly offset from the central bore by at least 8 mm.

According to aspects illustrated herein, there is disclosed a reverse shoulder prosthesis that includes a glenoid plate; a glenosphere; a humeral stem; a humeral adapter tray configured to sit near a resected surface of a humerus, the humeral adapter tray comprising: a cavity; a central bore; and a distal face including a boss, the boss: (i) configured as an extension of the distal face, (ii) posteriorly offset from the central bore by at least 10 mm, and (iii) configured to engage a humeral stem; and a humeral liner comprising: a distal rim configured to sit within the cavity of the humeral adapter tray; and a concave articulating surface configured to mate with a convex articulating surface of a glenosphere. In an embodiment, the boss, in addition to being posteriorly offset, is superiorly offset from the central bore by at least 8 mm.

According to aspects illustrated herein, there is disclosed a reverse shoulder prosthesis that includes a humeral adapter tray configured to sit near a resected surface of a humerus, the humeral adapter tray comprising: a cavity; a central bore; and a distal face including a boss, the boss: (i) configured as an extension of the distal face, (ii) superiorly offset from the central bore by at least 8 mm, and (iii) configured to engage a humeral stem; and a humeral liner comprising: a distal rim configured to sit within the cavity of the humeral adapter tray; and a concave articulating surface configured to mate with a convex articulating surface of a glenosphere.

In an embodiment, a humeral adapter tray of the present invention includes a boss that is posteriorly offset from the center of the humeral adapter tray by a distance ranging from at least 10 mm to 25 mm. In an embodiment, the boss is posteriorly offset from the center of the humeral adapter tray by a distance ranging from at least 12 mm to 24 mm. In an embodiment, the boss is posteriorly offset from the center of the humeral adapter tray by a distance ranging from at least 14 mm to 22 mm. In an embodiment, the boss is posteriorly offset from the center of the humeral adapter tray by a distance ranging from at least 16 mm to 20 mm. In an embodiment, the boss is posteriorly offset from the center of the humeral adapter tray by 18 mm. In an embodiment, the boss is posteriorly offset from the center of the humeral adapter tray by 22 mm. In an embodiment, the boss is posteriorly offset from the center of the humeral adapter tray by 25 mm.

In an embodiment, a humeral adapter tray of the present invention includes a boss that is superiorly offset from the center of the humeral adapter tray by a distance ranging from at least 8 mm to 25 mm. In an embodiment, the boss is superiorly offset from the center of the humeral adapter tray by a distance ranging from at least 9 mm to 24 mm. In an embodiment, the boss is superiorly offset from the center of the humeral adapter tray by a distance ranging from at least 10 mm to 23 mm. In an embodiment, the boss is superiorly offset from the center of the humeral adapter tray by a distance ranging from at least 11 mm to 20 mm. In an embodiment, the boss is superiorly offset from the center of the humeral adapter tray by 8 mm. In an embodiment, the boss is superiorly offset from the center of the humeral adapter tray by 10 mm. In an embodiment, the boss is superiorly offset from the center of the humeral adapter tray by 12 mm.

The boss of a humeral adapter tray of the present invention may be inserted into a humeral stem and attached to the stem using either a torque defining screw, a screw, or other fastening device positioned through the boss. A humeral adapter tray of the present invention can mate with a primary press-fit, primary cemented, and cemented revision/long stem humeral stems and reverse shoulder components, including, but not limited to, components of the Equinoxe® reverse shoulder assembly.

In an embodiment, a posterior/superiorly offset humeral tray of the present invention shifts the center of rotation posteriorly to better tension and increase the rotator moment arms of the remaining rotator cuff muscles to facilitate internal and external rotation.

In an embodiment, an implanted humeral adapter tray of the present invention increases the external rotator moment arms of the posterior rotator cuff in order to improve the function of the external rotators with reverse shoulder.

BRIEF DESCRIPTION OF THE DRAWINGS

The presently disclosed embodiments will be further explained with reference to the attached drawings. The drawings shown are not necessarily to scale, with emphasis instead generally being placed upon illustrating the principles of the presently disclosed embodiments.

FIG. 1A shows the latissimus dorsi; FIG. 1B shows the teres major; FIG. 1C shows the pectoralis major; and FIG. 1D shows the subscapularis.

FIGS. 5A, 5B and 5C show three views of an embodiment of a humeral liner of the present invention.

FIGS. 11A and 11B show a reverse shoulder assembly of the present invention. The posterior/superior offset humeral adapter tray of FIGS. 10A and 10B is being used with various other components of the Equinoxe® reverse shoulder assembly shown in FIG. 3 (the posterior/superior offset humeral adapter tray is used in lieu of the non-offset humeral tray).

FIGS. 19A and 19B show a comparison of the standard and posterior/superior offset reverse shoulder moment arms: infraspinatus (FIG. 19A) and the teres minor (FIG. 19B) abductor moment arms (y-axis) from 0 to 140° abduction in the scapular plane (x-axis).

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

As used herein, the term "deltoid wrapping" refers to a measure of the amount of wrapping of the deltoid around the greater tuberosity of the humerus, the angle defines the amount of abduction in the humeral plane required prior to when the deltoid stops wrapping the greater tuberosity.

As used herein, "muscle tensioning" of each muscle is measured as a comparison of muscle length for each joint configuration over a given type of motion relative to the muscle length for a normal shoulder over the same type of motion.

Muscles generate straight-line forces that are converted to torque in proportion to the perpendicular distance between the joint center of rotation and the muscle's line of action. As used herein, this perpendicular distance is referred to as the "muscle moment arm".

Figure 1A:
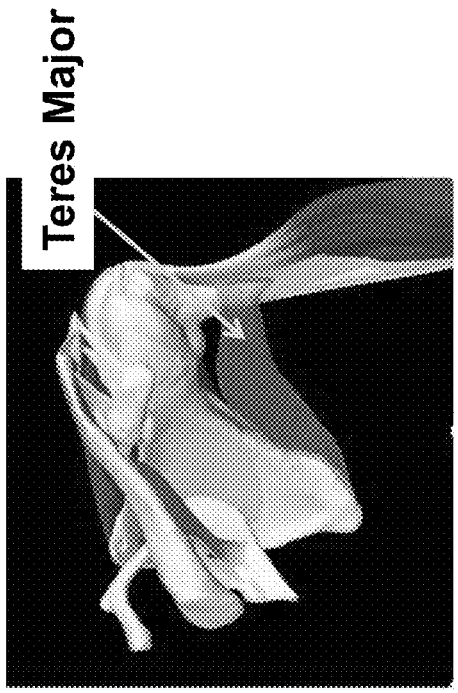
FIGS. 1A, 1B, 1C and 1D show views of the four internal rotator muscles of the chest.
Figure 1C:
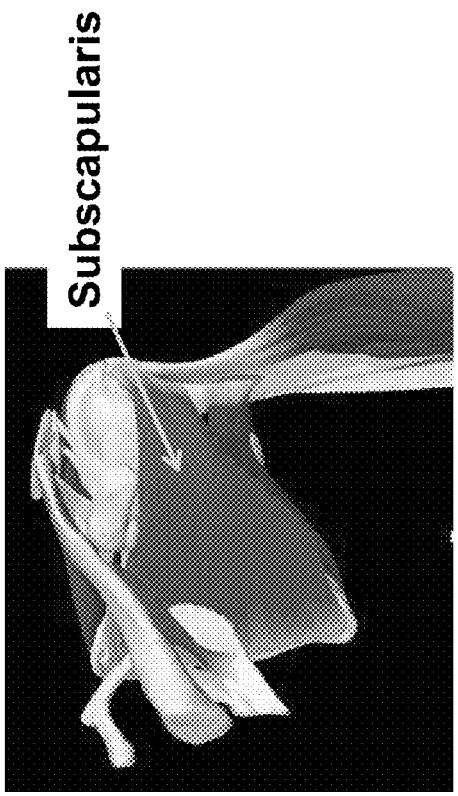
Figure 1B:
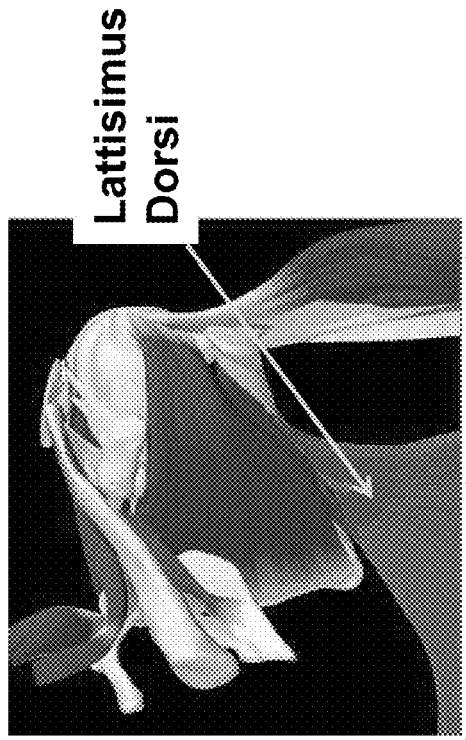
Figure 1D:
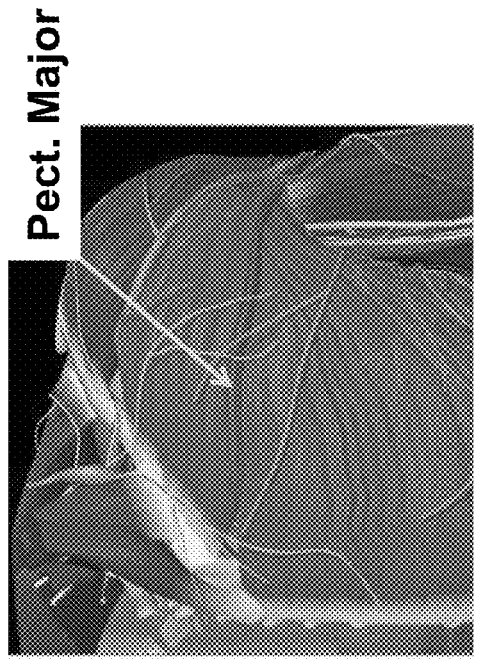

Loss of external rotation (and excessive internal rotation) impairs a patient's ability to maintain their arm in neutral rotation as the arm is elevated (e.g. positive horn blower's sign), preventing numerous activities of daily living including: shaking of hands, drinking/eating, and washing of hair. The origin of the latissimus dorsi muscle, illustrated in FIG. 1A, is the ribcage and its insertion is at the anterior humerus below the surgical neck. The origin of the teres major, illustrated in FIG. 1B, is the posterior scapulus and its insertion is at the anterior humerus below the surgical neck. The origin of the pectoralis major, illustrated in FIG. 1C, is at the ribcage and medial clavicle and its insertion is at the anterior humerus below the surgical neck. The origin of the subscapularis, illustrated in FIG. 1D, is at the anterior scapula and its insertion is at the lesser tuberosity.

Muscle transfers are often recommended in reverse shoulder patients with external rotation deficiency because the posterior deltoid alone is insufficient to restore active external rotation, even with lateralized reverse shoulder designs. In general, internal rotation muscles (e.g. muscles that attach to the anterior side of the humerus) are transferred across the joint center of rotation to the posterior side of the humerus where their contraction now causes external rotation. The latissimus dorsi is the most common muscle transferred in reverse shoulder arthroplasty, it is detached from the anterior shaft of the humerus and reattached to the greater tuberosity. Another common muscle transfer is a modification of L'Episcopo method in which both the latissimus dorsi and the teres major are transferred to the greater tuberosity. While muscle transfers have been demonstrated to successfully restore active external rotation, they should not be performed if the teres minor is functional. Additionally, it should be recognized that such procedures limit active internal rotation and further alter the relationship of each shoulder muscle to its normal physiologic function.

Figure 2B:
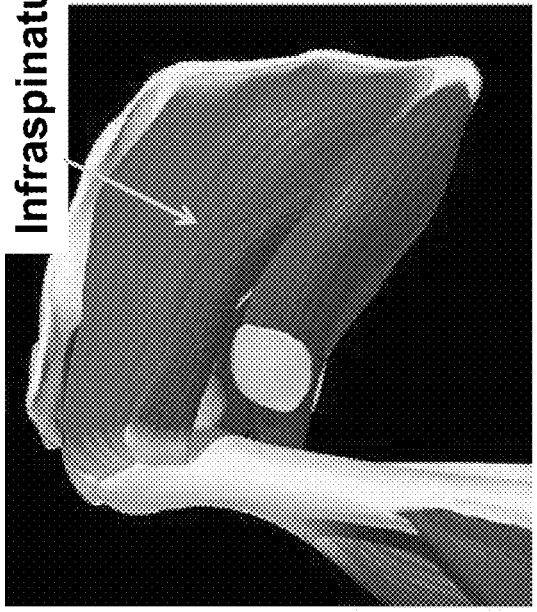
FIGS. 2A, 2B and 2C show views of the two external rotator muscles of the chest, the teres minor (FIG. 2A) and the infraspinatus (FIG. 2B) and the deltoid FIG. 2C.
Figure 2A:
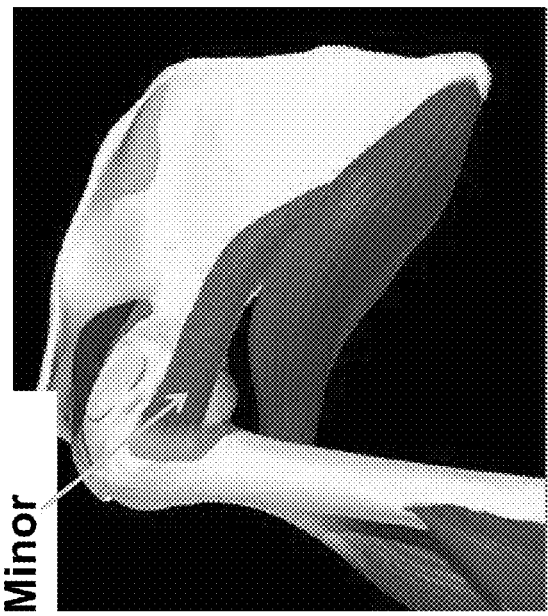
Figure 2C:
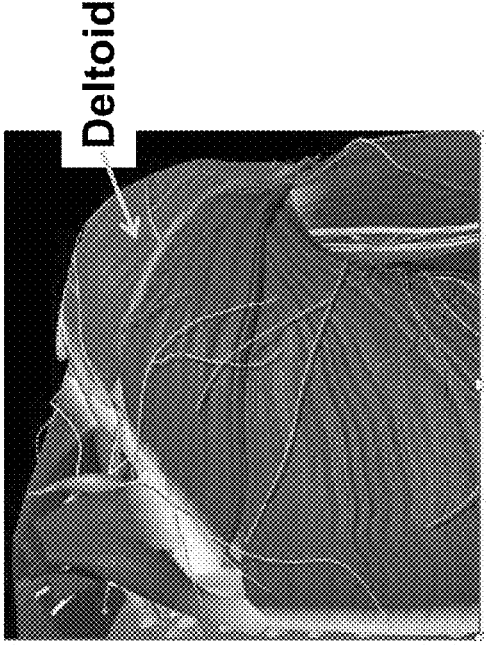

FIGS. 2A-2C show views of the two external rotator muscles of the chest, the teres minor (FIG. 2A) and the infraspinatus (FIG. 2B) and the deltoid FIG. 2C. The origin of the teres minor, illustrated in FIG. 2A, is at the lateral border of the scapula and its insertion is at the inferior portion of the greater tuberosity. The origin of the infraspinatus, illustrated in FIG. 2B, is at the posterior scapula and its insertion is at the superior portion of the greater tuberosity.

Figure 3:
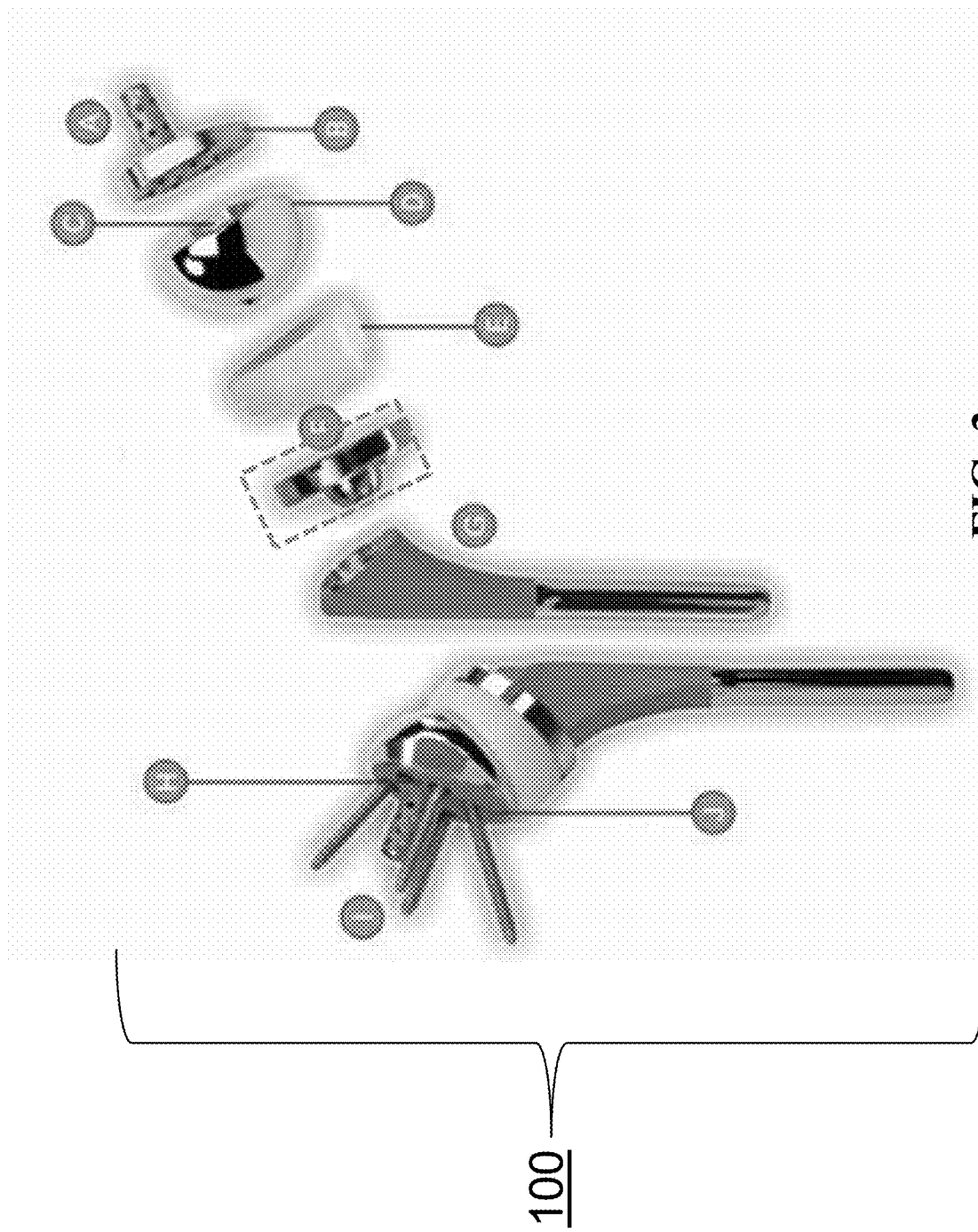
FIG. 3 shows the components of an Equinoxes reverse shoulder assembly manufactured by Exactech, Inc., in Gainesville, Fla. with a "non-offset" humeral adapter tray.
Figures 4A, 4B, 4C, 4D:
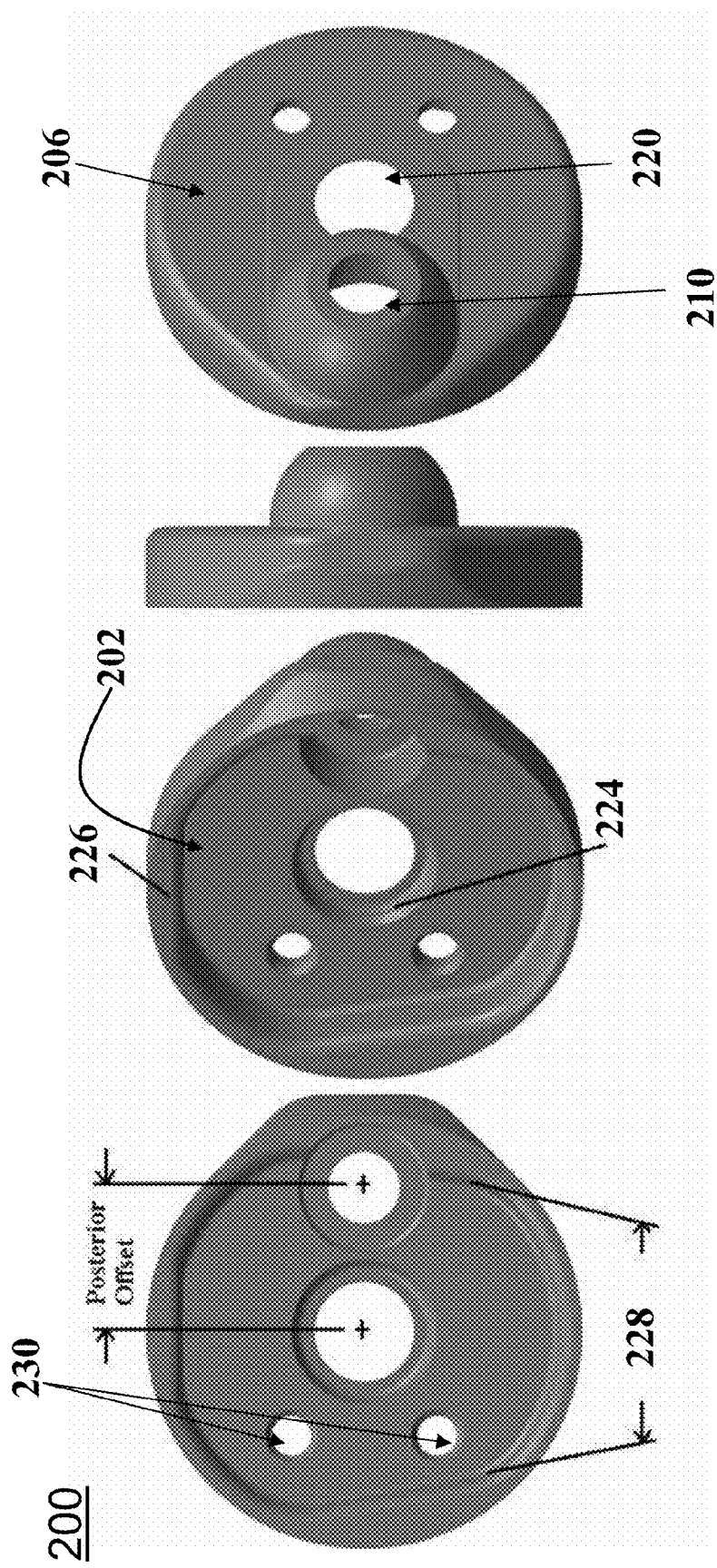
FIGS. 4A, 4B, 4C and 4D show four views of an embodiment of a posterior offset humeral adapter tray of the present invention. The posterior offset humeral adapter tray can be used instead of the non-offset humeral adapter tray of the Equinoxe® reverse shoulder assembly shown in FIG. 3.
Figures 6A, 6B, 6C:
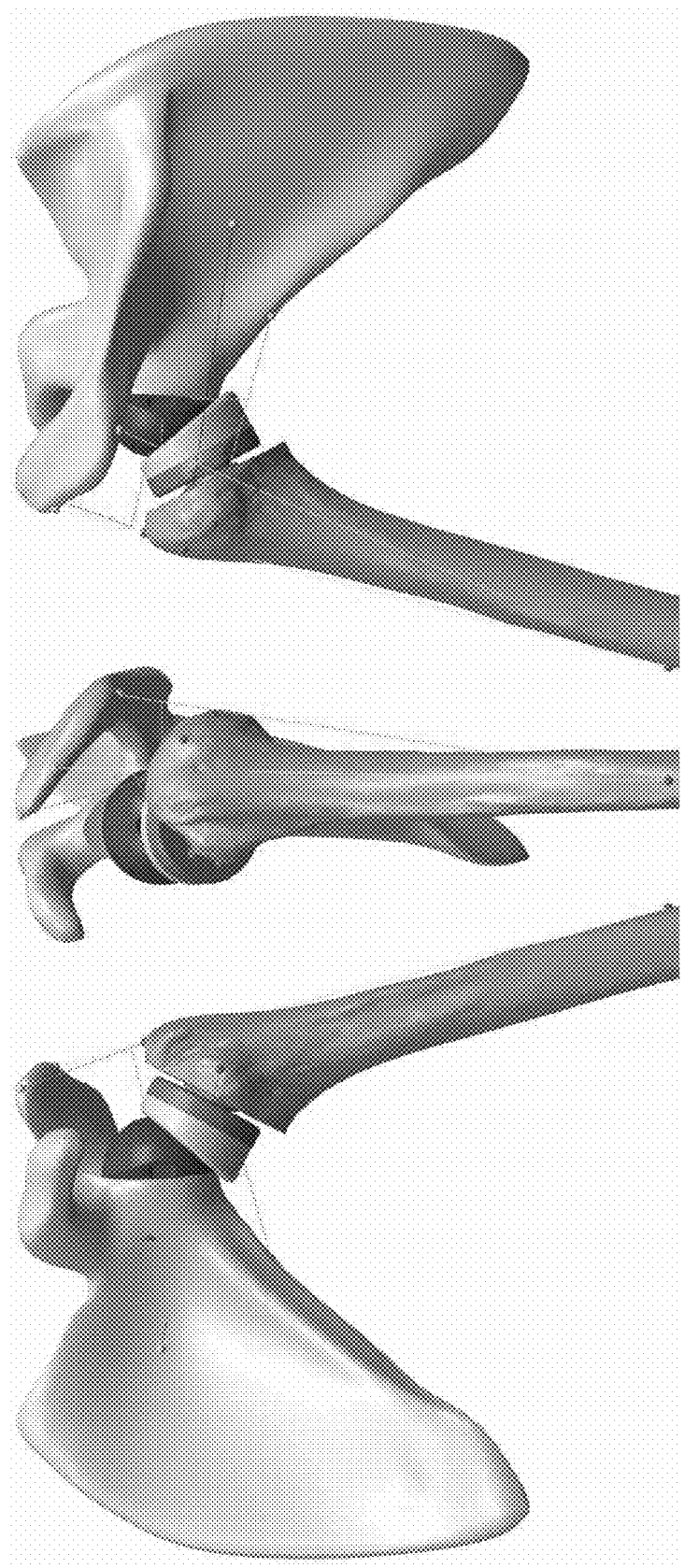
FIGS. 6A, 6B and 6C show a computer muscle model assembly of the posterior offset humeral adapter tray of FIGS. 4A-D implanted in a humerus when the arm is abducted at about 15° in the scapular plane. As illustrated, the humeral adapter tray is configured to sit near a resected surface of a humerus.
Figure 7:
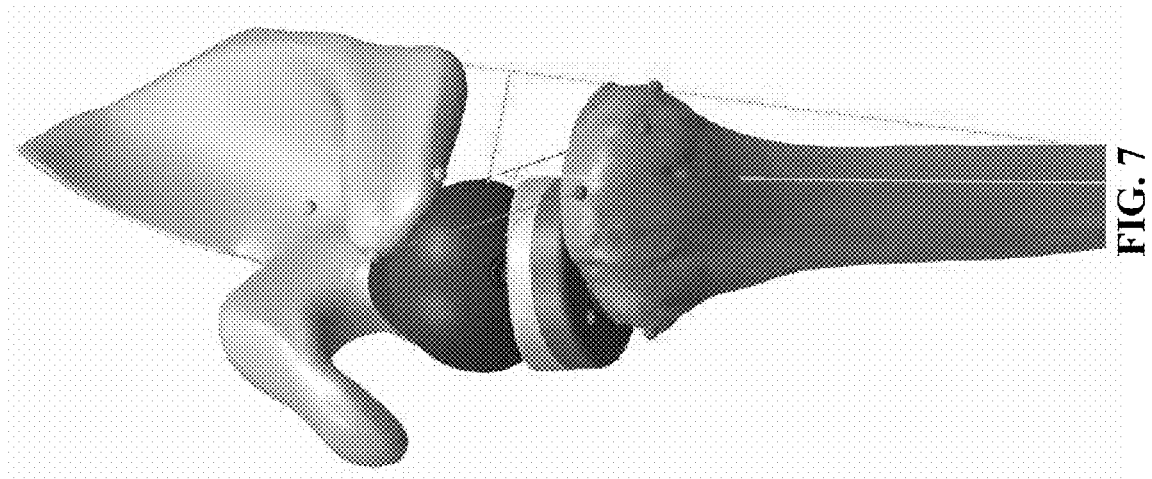
FIG. 7 shows a computer muscle model assembly of increased length in the posterior rotator cuff rotator moment arm when the posterior offset humeral adapter tray of FIG. 4 is implanted in a humerus. As illustrated, the humeral adapter tray is configured to sit near (above) a resected surface of a humerus.

FIG. 3 shows components of the Equinoxe® standard reverse shoulder assembly 100 manufactured by Exactech, Inc., in Gainesville, Fla. The Equinoxe® standard reverse shoulder assembly 100 includes (a) a bone cage which may improve glenoid fixation and allow bone "through-growth" using inductive/conductive bone grafts; (b) an inferiorly shifted glenoid plate which may allow fixation to occur in the center of the glenoid while also ensuring inferior glenosphere overhang, thereby, eliminating/minimizing scapular notching; (c) a glenosphere (in an embodiment, a chamfered glenosphere) which may aid in glenosphere insertion and protects any remaining intact soft tissues; (d) an extended glenosphere articular surface which may improve range of motion and maximize glenosphere inferior overhang to minimize the potential for scapular notching; (e) multiple humeral liner (standard and constrained), humeral adapter tray (with boss centered, i.e., non-offset) and glenosphere options which provide intra-operative flexibility; (f) anti-rotation features on humeral liners improve implant connection and stability; (g) platform humeral stem facilitates a revision of a primary Equinoxe® humeral stem to a reverse. Locking caps lock compression screws to the glenoid plate at a variable angle (not pictured); (h) the curved back glenosphere/glenoid plate may conserve bone and convert shear forces to compressive forces; (i) variable angle compression screws may compress the glenoid plate to the bone while providing 30 degrees of angular variability; and (j) an anatomical-shaped glenoid plate which may provide multiple options for screw insertion, which is particularly important when revising a pegged and/or keeled glenoid to a reverse. Torque defining screw locks the humeral adapter tray at 11 N*m (not pictured).

FIGS. 4A-4D show an embodiment of a posterior offset humeral adapter tray 200 of the present invention. The humeral adapter tray 200 includes a cavity 202 which is non-circular shaped and configured to accept a humeral liner so as to result in rotational stability. The humeral adapter tray 200 includes a distal face 204 having a boss 210, which is configured as an extension of the distal face. The boss 210 is a knob, stud or other protuberance or extension, The boss 210 is posteriorly offset from the center of the humeral adapter tray 200 by at least 10 mm. In an embodiment, the boss 210 is posteriorly offset from the center of the humeral adapter tray 200 by at least 10 mm. In an embodiment, the boss 210 is posteriorly offset from the center of the humeral adapter tray 200 a distance ranging from 11 mm to 25 mm. In an embodiment, the boss 210 is posteriorly offset from the center of the humeral adapter tray 200 a distance ranging from 12 mm to 24 mm. In an embodiment, the boss 210 is posteriorly offset from the center of the humeral adapter tray 200 a distance ranging from 14 mm to 22 mm. In an embodiment, the boss 210 is posteriorly offset from the center of the humeral adapter tray 200 a distance ranging from 16 mm to 20 mm. In an embodiment, the boss 210 is posteriorly offset from the center of the humeral adapter tray 200 by 18 mm. In an embodiment, the boss 210 is posteriorly offset from the center of the humeral adapter tray 200 by 22 mm. In an embodiment, the boss 210 is posteriorly offset from the center of the humeral adapter tray 200 by 25 mm. In an embodiment, the posterior offset humeral adapter tray 200 is constructed from titanium. In an embodiment, the humeral adapter tray 200 is machined from wrought Ti-6Al-4V. In an embodiment, the humeral adapter tray 200 features a dual locking mechanism which comprises a female locking mushroom 224 and a lateral male dove tail feature 226. In an embodiment, the humeral adapter tray 200 has an anti-rotation feature 228. The anti-rotation feature 228 is an asymmetrically shaped female angled surface on the humeral adapter tray 200—its intent is to prevent rotation motion between the humeral liner 250 and humeral tray 200. In an embodiment, the humeral adapter tray 200 has both a dual locking mechanism and anti-rotation feature.

FIGS. 5A, 5B and 5C show three views of an embodiment of a humeral liner 250 of the present invention. The humeral liner 250 is a concave component which mates with a convex glenosphere. The humeral liner 250 includes a distal rim 252 which is configured to position within the cavity 202 of the humeral adapter tray 200 so as to result in rotational stability. In an embodiment, the distal rim 252 has a non-circular shape configured to mate with the non-circular shape of the cavity 202 of the humeral adapter tray 200. In an embodiment, the humeral liner 250 features a dual locking mechanism which comprises a male locking mushroom 254 and a lateral female dove tail feature 256. In an embodiment, the humeral liner 250 features an anti-rotation base 258. The anti-rotation feature 258 is an asymmetrically shaped male angled surface on the humeral liner 250—its intent is to prevent rotation motion between the humeral liner 250 and humeral tray 200. In an embodiment, the humeral liner 250 features both a dual locking mechanism and an anti-rotation base. In an embodiment, the humeral liner 250 is machined from compression molded UHMWPE.

The posterior offset humeral adapter tray 200 can be attached to a humeral stem, for example an Equinoxe® humeral stem, using a torque defining screw that clamps the humeral adapter tray 200 to the humeral stem. The torque defining screw is positioned through the boss 210 on the cavity 202 side of the humeral adapter tray 200. A humeral liner 250, for example an Equinoxe® humeral liner, is attached to the posterior offset humeral adapter tray via the center bore 220. Holes 230 in the humeral adapter tray 200 attach to an instrument to provide counter-torque. The posterior offset humeral adapter tray 200 posteriorly shifts the boss 210 to increase the external rotation moment arms of the posterior rotator cuff. Increasing the external rotation moment arms of the posterior rotator cuff has the potential to improve the function for patients with functioning, but weak external rotators (e.g. patients with a nonfunctional infraspinatus but a functional teres minor), which is common in patients with rotator cuff tear arthropathy.

A computer muscle model was conducted to evaluate the effect of the posterior offset humeral adapter tray 200 of the present invention (as part of an Equinoxe® reverse shoulder assembly) on the muscle lengthening/shortening, deltoid elongation, and moment arms of the anterior and posterior rotator cuff as the posterior offset humeral adapter tray was abducted in the scapular plane (relative to a non-offset reverse shoulder humeral adapter tray of the Equinoxe® standard reverse shoulder assembly). Five muscles were simulated in this analysis: middle deltoid, posterior deltoid, subscapularis, infraspinatus, and teres minor; the center of each muscle's attachment on the humerus and scapula were digitized on each bone model and a line was drawn to connect each point to simulate each muscle. After assembly, each assembly was abducted in the scapular plane and evaluated relative to a normal shoulder by quantifying each muscle's abductor moment arm, each muscle's length, and each muscle's line of action. Muscle lengths were measured directly in Unigraphics. Abductor moment arms were calculated using Matlab (Mathworks, Inc.) in Matlab, the scapula was rotated in the scapular plane 1° for every 1.8° of humeral motion in the scapular plane.

Figures 8A, 8B, 8C:
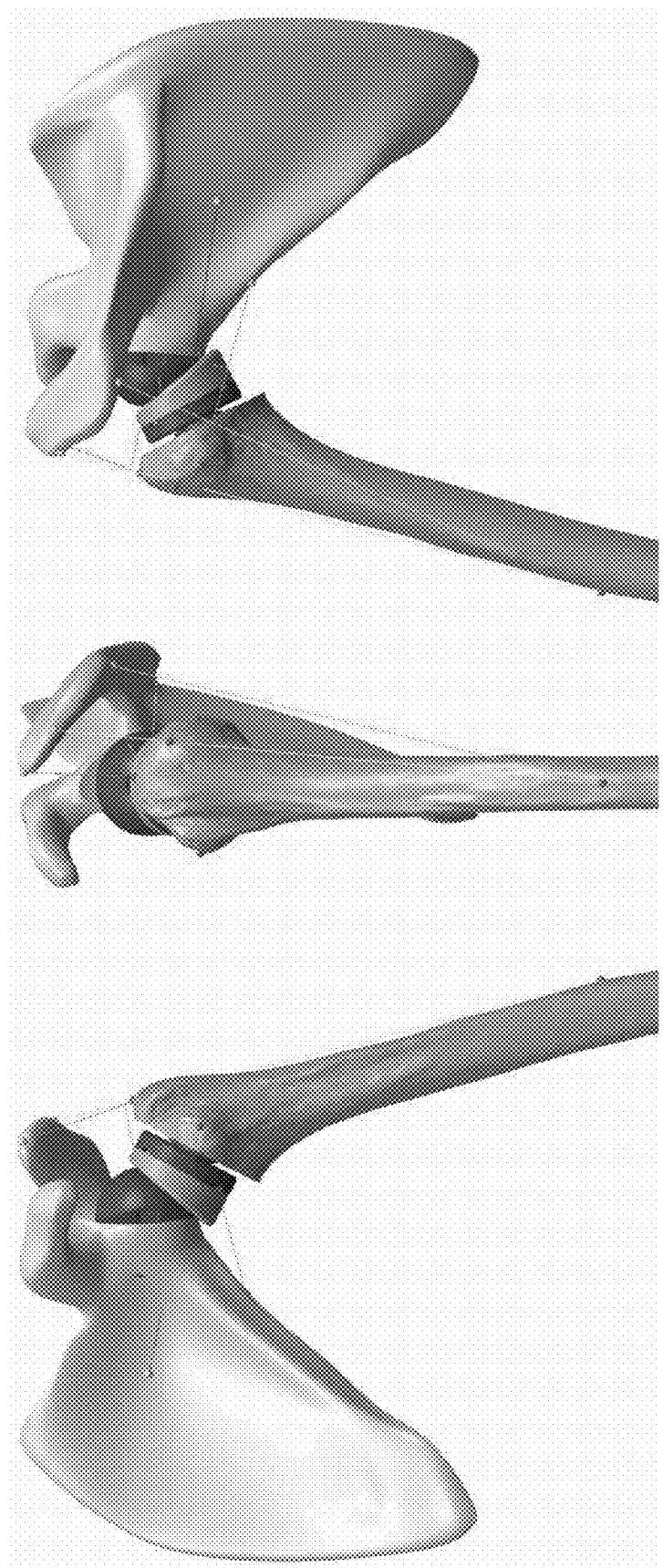
FIGS. 8A, 8B and 8C show a computer muscle model assembly of a non-offset reverse shoulder humeral adapter tray implanted in a humerus when the arm is abducted at about 15° in the scapular plane. As illustrated, the humeral adapter tray is configured to sit near (above) a resected surface of a humerus.
Figures 9A, 9B, 9C:
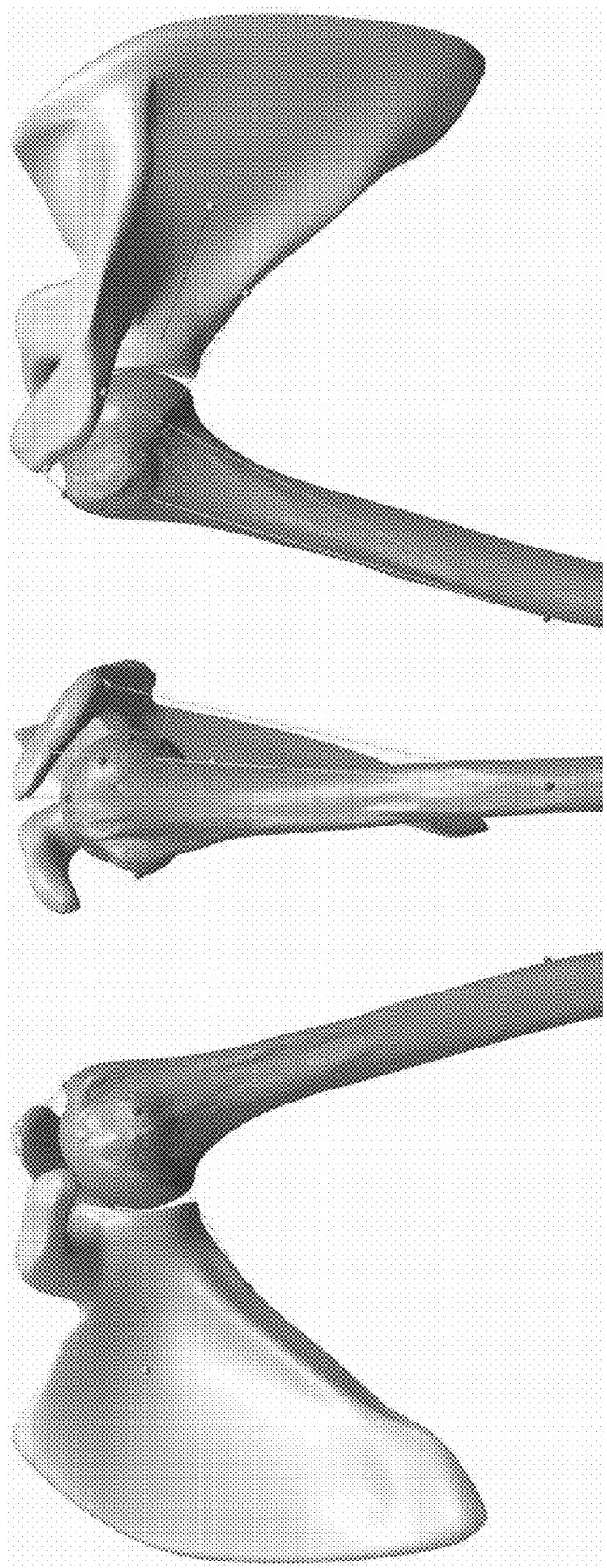
FIGS. 9A, 9B and 9C show a computer muscle model assembly of the normal shoulder when the arm is abducted at about 15° in the scapular plane.

As described in Table 1, the computer model demonstrated that a posterior offset humeral adapter tray of the present invention (FIGS. 6A-6C and FIG. 7), having a boss that is posteriorly offset by 10 mm, better restored the anatomic tension of the infraspinatus (from −2.2% to 1.2% of normal muscle length) and teres minor (from −5.9% to −0.9% of normal muscle length) relative to a non-offset humeral adapter tray (FIGS. 8A-8C) when assembled to the 38 mm Equinoxe® reverse shoulder. Note that FIGS. 6A-6C and FIG. 7 depict the offset humeral adapter tray as it is abducted at about 15° in the scapular plane, and FIGS. 8A-8C depicts a non-offset humeral adapter tray as it is abducted at about 15° in the scapular plane. For comparative purposes, FIGS. 9A-9C depict a normal shoulder abducted at about 15° in the scapular plane. As described in Table 2, the posterior offset humeral adapter tray of the present invention, having a boss that is posteriorly offset by 10 mm, increased the external rotator moment arms of the posterior deltoid by 2%, infraspinatus by 45%, and teres minor by 18% relative to the increases associated with a nonoffset humeral adapter tray over a normal shoulder.

TABLE 1

Average Anterior and Posterior Rotator Cuff Muscle Elongation Relative to a Normal Shoulder as the Humerus is Elevated in the Scapular Plane from 0 to 60 degrees (relative to a fixed scapula)

| Implant Configuration | Subscapularis | Infraspinatus | Teres Minor |
|---|---|---|---|
| 38 Equinoxe ® (nonoffset humeral tray) | 2.4% | −2.2% | −5.9% |
| 38 Equinoxe ® (10 mm posteriorly offset humeral tray - FIG. 4) | −1.8% | 1.2% | −0.9% |
| Difference | −4.2% | 3.4% | 5% |

TABLE 2

Average Rotator Moment Arm Length Relative to a Normal Shoulder for Varying Reverse Shoulder as the Humerus is Elevated in the Scapular Plane from 0 to 60 degrees (relative to a fixed scapula)

| Implant Configuration | Subscapularis | Infraspinatus | Teres Minor | Posterior Deltoid |
|---|---|---|---|---|
| 38 Equinoxe ® (nonoffset humeral tray) | −58% | −4% | −25% | 18% |
| 38 Equinoxe ® (posteriorly offset humeral tray - FIG. 4) | −90% | 41% | −7% | 20% |
| Difference | −32% | 45% | 18% | 2% |

In an embodiment, a reverse shoulder humeral tray of the present disclosure is used in a reverse shoulder prosthesis that may include at least some of the following components, a humeral stem (which may be used in pressfit and/or cemented applications and may be constructed from titanium), a humeral liner (a concave component which mates with a convex glenosphere; may be constructed from UHMWPE), a glenosphere (may be constructed from cobalt chrome), an adjustment plate (may be constructed from titanium), a locking plate (may be constructed from titanium) and a glenoid plate (may be constructed from titanium), and a number of screws and fixations devices for assembly of the individual components to one another and for assembly of the construct to the native bone (all may be constructed from titanium).

Figures 10A, 10B:
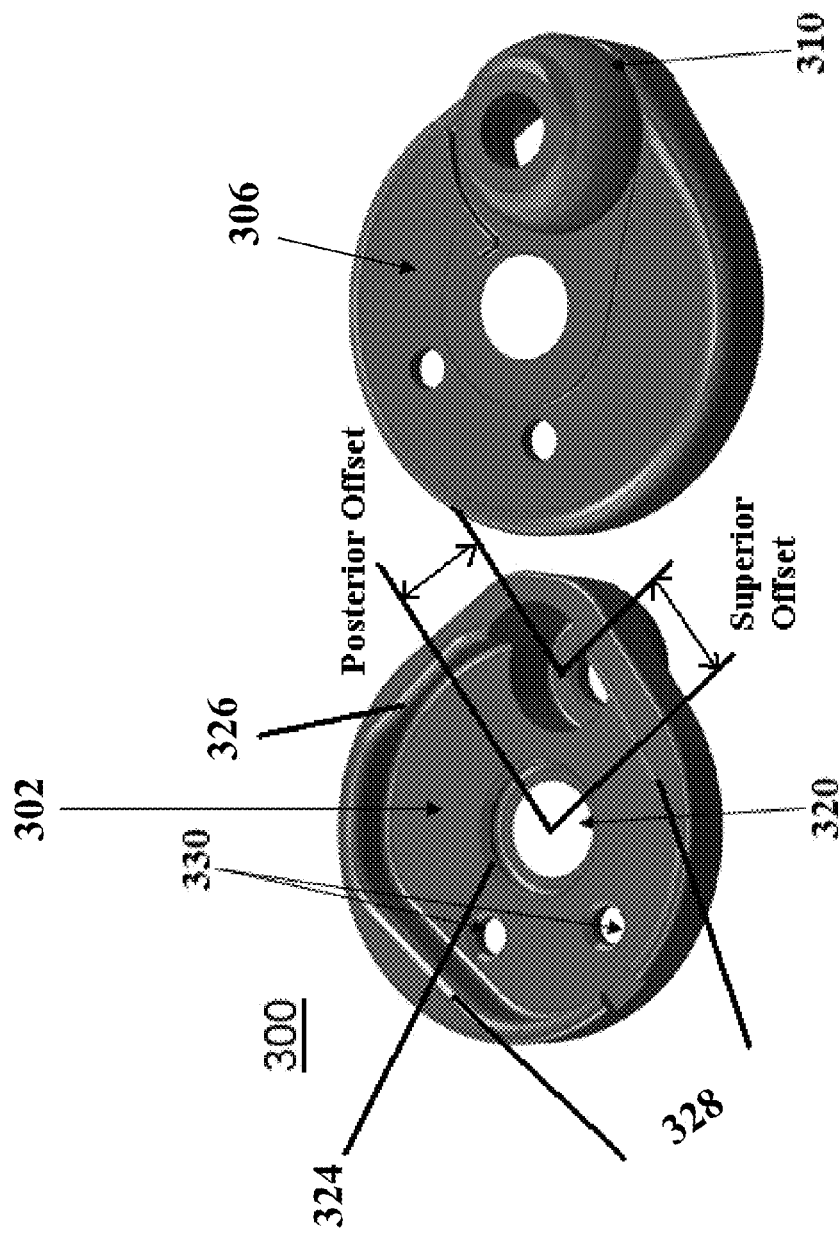
FIGS. 10A and 10B show two views of an embodiment of a posterior/superior offset humeral adapter tray of the present invention. The posterior/superior offset humeral adapter tray can be used instead of the non-offset humeral adapter tray of the Equinoxe® reverse shoulder assembly shown in FIG. 3.

FIGS. 10A and 10B show an embodiment of a posterior/superior offset humeral adapter tray 300 of the present invention. The humeral adapter tray 300 includes a cavity 302 which is non-circular shaped and configured to accept a humeral liner so as to result in rotational stability. The humeral adapter tray 300 includes a distal face 304 having a boss 310, which is configured as an extension of the distal face. The boss 310 is a knob, stud or other protuberance or extension. In an embodiment, the boss 310 is posteriorly offset from the center of the humeral adapter tray 300 by at least 10 mm. In an embodiment, the boss 310 is posteriorly offset from the center of the humeral adapter tray 300 by about 11 mm to about 25 mm. In an embodiment, the boss 310 is posteriorly offset from the center of the humeral adapter tray 300 by about 12 mm to about 24 mm. In an embodiment, the boss 310 is posteriorly offset from the center of the humeral adapter tray 300 by about 14 mm to about 22 mm. In an embodiment, the boss 310 is posteriorly offset from the center of the humeral adapter tray 300 by about 16 mm to about 20 mm. In an embodiment, the boss 310 is posteriorly offset from the center of the humeral adapter tray 300 by about 18 mm. In an embodiment, the boss 310 is posteriorly offset from the center of the humeral adapter tray 300 by about 22 mm. In an embodiment, the boss 310 is posteriorly offset from the center of the humeral adapter tray 300 by about 25 mm. In an embodiment, the boss 310 is superiorly offset from the center of the humeral adapter tray 300 by at least 8 mm. In an embodiment, the boss is superiorly offset from the center of the humeral adapter tray 300 by a distance ranging from at least 8 mm to 25 mm. In an embodiment, the boss is superiorly offset from the center of the humeral adapter tray 300 by a distance ranging from at least 9 mm to 24 mm. In an embodiment, the boss is superiorly offset from the center of the humeral adapter tray 300 by a distance ranging from at least 10 mm to 23 mm. In an embodiment, the boss is superiorly offset from the center of the humeral adapter tray 300 by a distance ranging from at least 11 mm to 20 mm. In an embodiment, the boss is superiorly offset from the center of the humeral adapter tray 300 by 8 mm. In an embodiment, the boss is superiorly offset from the center of the humeral adapter tray 300 by 10 mm. In an embodiment, the boss is superiorly offset from the center of the humeral adapter tray 300 by 12 mm.

As illustrated in FIGS. 11A and 11B, the posterior/superior offset humeral adapter tray 300 can be attached to a humeral stem 400 of an Equinoxe® reverse shoulder assembly using a torque defining screw positioned through the boss 310. A glenosphere 500 of the Equinoxe® reverse shoulder assembly is also illustrated. A humeral liner 250, for example an Equinoxe® humeral liner, is attached to the posterior offset humeral adapter tray via the center bore. Holes in the humeral adapter tray 300 attach to an instrument to provide countertorque. The posterior offset humeral adapter tray 300 posteriorly shifts the boss 310 to increase the external rotation moment arms of the posterior rotator cuff. Increasing the external rotation moment arms of the posterior rotator cuff has the potential to improve the function for patients with functioning, but weak external rotators (e.g. patients with a nonfunctional infraspinatus but a functional teres minor), which is common in patients with rotator cuff tear arthropathy.

In an embodiment, the humeral adapter tray 300 is constructed from titanium. In an embodiment, the humeral adapter tray 300 is machined from wrought Ti-6Al-4V. In an embodiment, the humeral adapter tray 300 features a dual locking mechanism which comprises a female locking mushroom 324 and a lateral male dove tail feature 326. In an embodiment, the humeral adapter tray 300 has an anti-rotation feature 328. The anti-rotation feature 328 is an asymmetrically shaped female angled surface on the humeral adapter tray 300—its intent is to prevent rotation motion between the humeral liner 250 and humeral tray 300. In an embodiment, the humeral adapter tray 300 has both a dual locking mechanism and anti-rotation feature.

Figure 12:
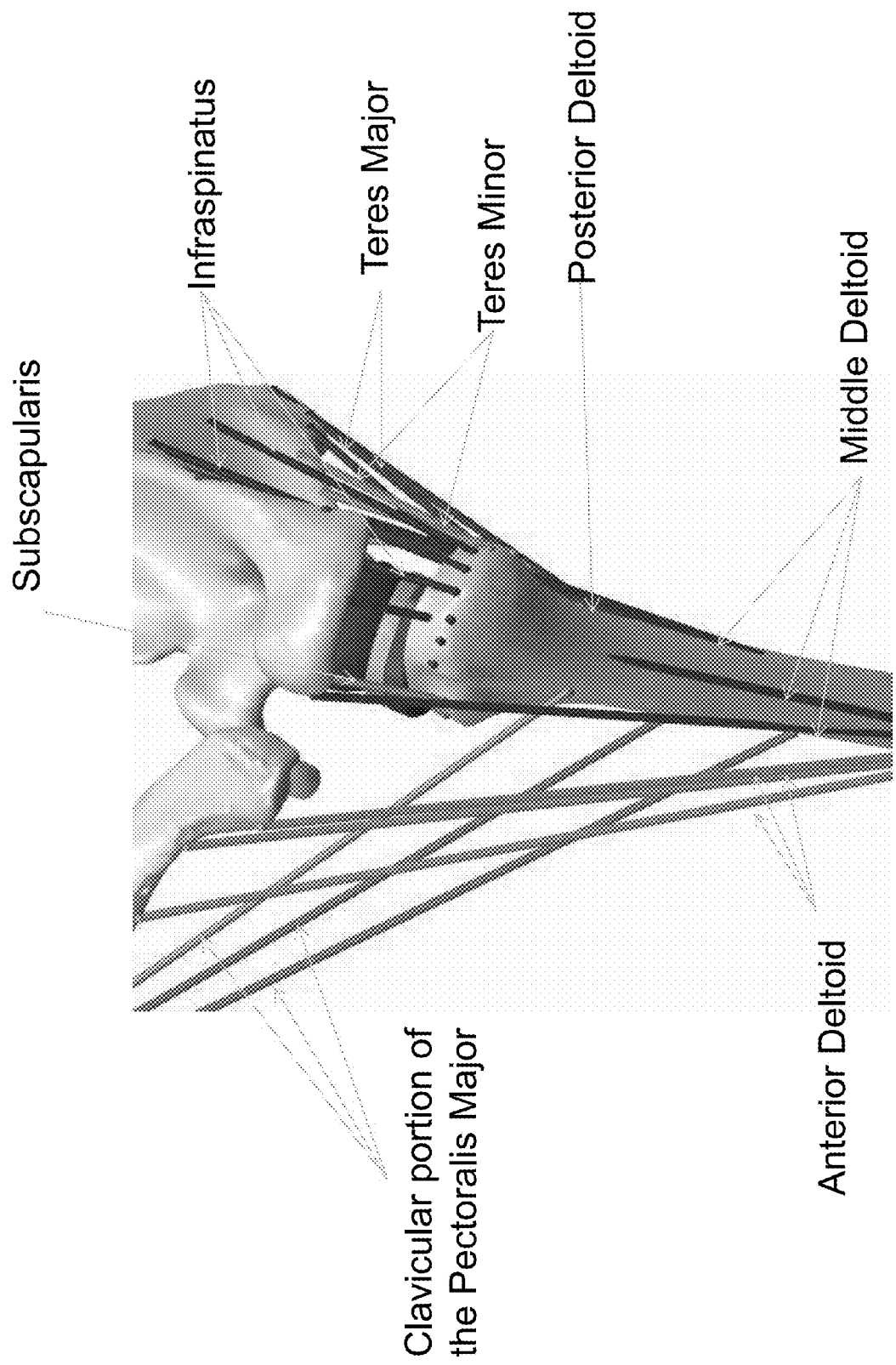
FIG. 12 shows superior-inferior view of the reverse shoulder assembly of FIG. 11 in a computer muscle model. Note the more posteriorly shifted position of the humeral tuberosities. As illustrated, the humeral adapter tray is configured to sit near (above) a resected surface of a humerus.

The posterior/superior offset humeral adapter tray 300 translates the humeral head and tuberosities posteriorly (FIG. 12) to better tension the posterior rotator cuff muscles and increase their external moment arm (to improve the torque capability) and translates the humeral head and tuberosities superiorly to reduce the over-tensioning of the deltoid (as occurs with reverse shoulder arthroplasty).

Figures 13A, 13B:
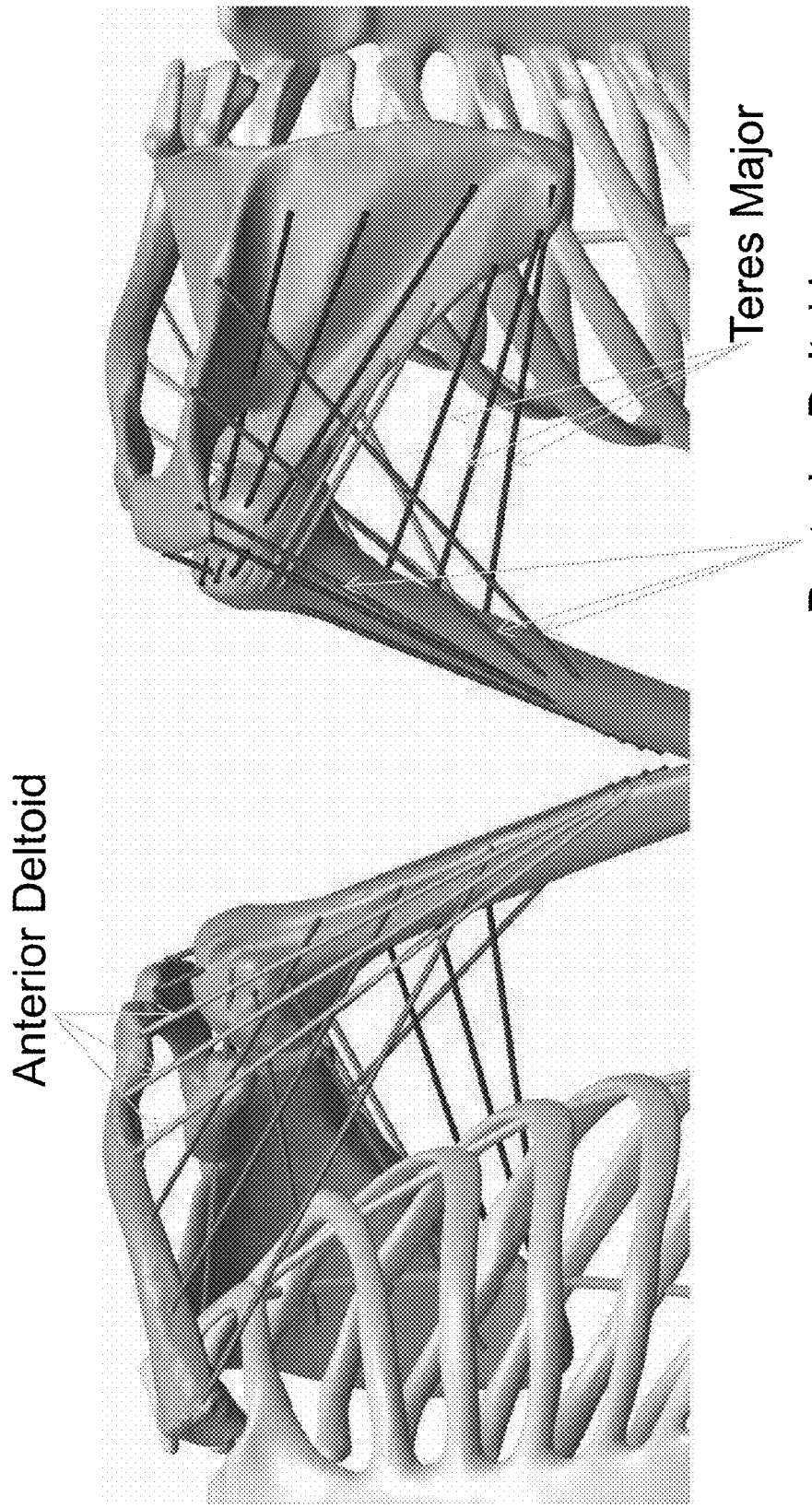
FIGS. 13A and 13B show a computer model of 8 muscles simulated as 3 lines from origin to insertion, anterior (left) and posterior (right) views of the normal shoulder at 25° abduction in the scapular plane.

A 38 mm Equinoxe® standard reverse shoulder assembly (having the nonoffset humeral adapter tray) and a 38 mm Equinoxe® offset reverse shoulder assembly (having a boss that is posteriorly offset by 11 mm and superiorly offset by 9 mm) was geometrically modeled and implanted in a 3-D digitized scapula and humerus; a 3-D digital clavicle and ribcage were also included (Pacific Research Laboratories, Inc; Vashon Island, Wash.). The digital humerus and scapula were assembled to simulate a normal shoulder, functioning as the control in this analysis; the humeral head was centered on the glenoid and offset by 4 mm from the center of the glenoid to account for the thickness of the cartilage and labrum. Eight muscles were simulated as 3 lines from its origin on the scapula or clavicle to its insertion on the humerus: anterior deltoid, middle deltoid, posterior deltoid, subscapularis, infraspinatus, teres major, teres minor, and the clavicular portion of the pectoralis major (FIG. 13A and FIG. 13B).

Figures 14A, 14B:
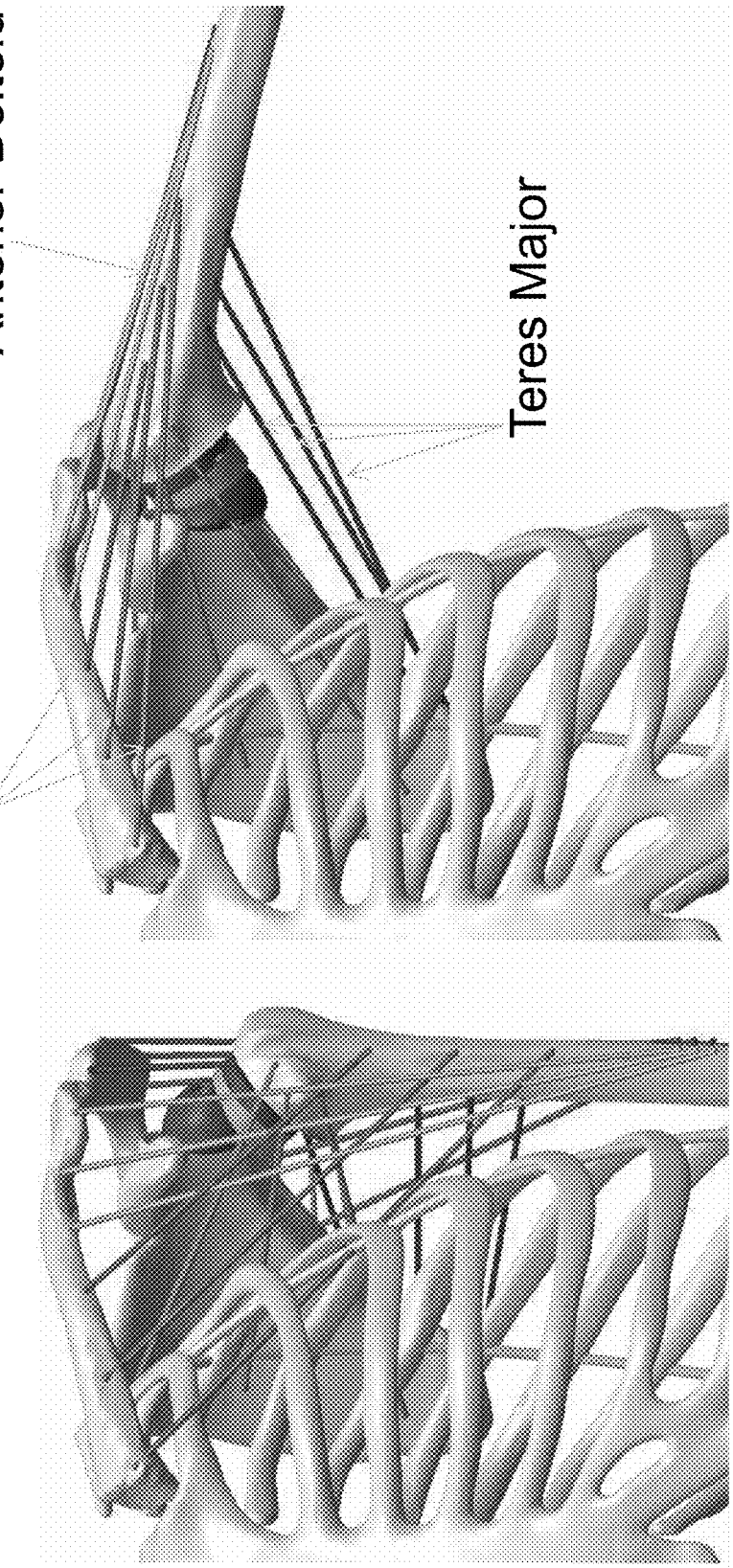
FIGS. 14A and 14B show a computer model simulating abduction of the reverse shoulder assembly of FIGS. 11A and 11B (0° tilt, 20° humeral retroversion) from 0 to 80° in the scapular plane relative to fixed scapula. As illustrated, the humeral adapter tray is configured to sit near (above) a resected surface of a humerus.
Figures 15A, 15B:
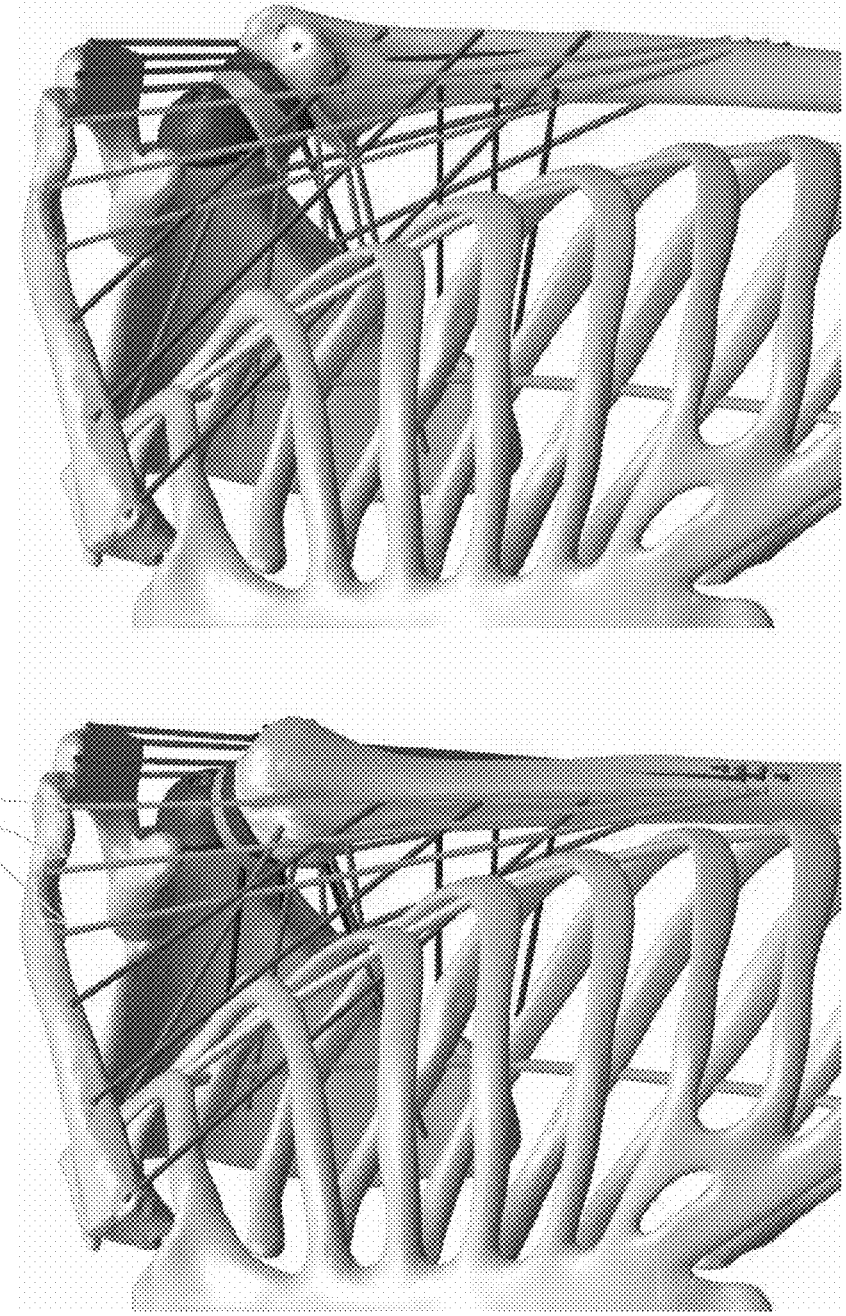
FIGS. 15A and 15B show a computer model simulating internal (left) and external (right) rotation of the reverse shoulder assembly of FIGS. 11A and 11B at 40° relative to fixed scapula. As illustrated, the humeral adapter tray is configured to sit near (above) a resected surface of a humerus.

To characterize the biomechanical impact of the 38 mm Equinoxe® offset reverse shoulder assembly (having a boss that is posteriorly offset by 11 mm and superiorly offset by 9 mm) on each muscle, each device was implanted identically on glenoid so that the glenoid baseplate aligns with the inferior glenoid rim as the humeral component was successively oriented at 20° retroversion. After assembly, 2 motions were simulated: 1) abduction (FIG. 14A and FIG. 14B) and 2) internal/external rotation (FIG. 15A and FIG. 15B). To simulate abduction, the humeral component was abducted from 0 to 80° in the scapular plane relative to a fixed scapula. To simulate internal/external rotation, the humeral component was rotated 40° internally and 40° externally with the arm at 0° abduction.

For each simulated motion, muscle lengths were measured as the average length of the 3 lines representing the muscle at each degree of motion; each average muscle length, at each degree of motion was compared as a percentage of the corresponding muscle length of the normal shoulder. To clarify, a positive percentage indicates elongation of the muscle relative to the normal shoulder; whereas, a negative percentage indicates shortening of the muscle relative to the normal shoulder. The angle of abduction in which the middle deltoid stops wrapping around the greater tuberosity was also quantified as a measure of stability (e.g. less deltoid wrapping implies reduced humeral head compression into the glenoid) for the normal shoulder and the standard and offset Equinoxe® reverse shoulders. Moment arms were calculated using a custom code in Matlab (Mathworks, Inc.). Abductor moment arms were calculated for each muscle in abduction from 0 to 140° (it should be noted that in Matlab, the scapula was rotated in the scapular plane 1° for every 1.8° of humeral motion in the scapular plane; whereas in Unigraphics the scapula remained fixed). Rotation moment arms were calculated for each muscle from −30 (IR) to 60° (ER) with the arm in 30° abduction.

As described in Table 3, both Equinoxe® reverse shoulders, regardless of humeral tray offset or position, shifted the center of rotation (CoR) medially and inferiorly relative to the normal shoulder. For the standard (non-offset humeral tray) this shift in the CoR caused a medial and inferior shift of the humerus and a decrease in the middle deltoid wrapping angle relative to the normal shoulder, see Table 4. For the offset humeral tray, the humerus was shifted superiorly and posteriorly relative to the non-offset humeral tray, see Tables 3 and 4.

TABLE 3

Change in Center of Rotation for Each Reverse Shoulder Relative to Normal Shoulder

| | Medial Shift in Center of Rotation ("CoR") | Inferior Shift in Center of Rotation ("CoR") | Posterior Shift of the Humerus |
|---|---|---|---|
| 38 mm Equinoxe ®, standard offset | 27.1 mm | 4.5 mm | 0 mm |

TABLE 3-continued

Change in Center of Rotation for Each Reverse Shoulder
Relative to Normal Shoulder

|  | Medial Shift in Center of Rotation ("CoR") | Inferior Shift in Center of Rotation ("CoR") | Posterior Shift of the Humerus |
|---|---|---|---|
| 38 mm Equinoxe ®, post/sup offset | 27.1 mm | 4.5 mm | 14.3 mm |

TABLE 4

Medial/Lateral Position of the Humerus and its
Impact on Deltoid Wrapping

|  | Lateral Distance from Coracoid to Greater Tuberosity with Humerus Abducted at 0° | Angle of Abduction which Middle Deltoid Stops Wrapping Greater Tuberosity | Distance from Bottom of Acromion to Top of the Greater Tuberosity |
|---|---|---|---|
| Normal Shoulder | 56.2 mm | 48° | 19.0 mm |
| 38 mm Equinoxe ®, standard offset | 47.1 mm | 40° | 53.8 mm |
| 38 mm Equinoxe ®, post/sup offset | 57.4 mm | >65° | 44.9 mm |

As described in Tables 5-7, for each simulated motion, both Equinoxe® reverse shoulders elongated each head of the deltoid, shortened the internal rotators (subscapularis and teres major, with the exception of the pectoralis major which was elongated) and shortened the external rotators (infraspinatus and teres minor) relative to the normal shoulder. As described in Table 5, in abduction, the Equinoxe® posterior/superior offset humeral tray reverse shoulder design over-tensioned the three heads of the deltoid less, tensioned the pectoralis more, and better restored the anatomic tension of the subscapularis, infraspinatus, teres major, and teres minor than the Equinoxe® standard (non-offset) humeral tray reverse shoulder design. Similar trends were observed during internal and external rotation, see Tables 6 and 7.

TABLE 5

Average Muscle Length Relative to Normal Shoulder as Each Reverse Shoulder is Abducted in the Scapular Plane from 0 to 65°. Note that the offset humeral tray impinged superiorly at 65° so the analysis range was reduced from 0 to 80°.

|  | Ant. Deltoid | Mid Deltoid | Post. Deltoid | Subscap | Infraspin | Teres Major | Teres Minor | Pec Major |
|---|---|---|---|---|---|---|---|---|
| 38 mm Equinoxe ®, standard offset | 8.8% | 9.8% | 7.5% | −0.7% | −2.9% | −1.9% | −5.7% | 5.9% |
| 38 mm Equinoxe ®, post/sup offset | 7.3% | 6.0% | 4.7% | 0.5% | 0.4% | −1.0% | 0.3% | 8.5% |

TABLE 6

Average Muscle Length Relative to Normal Shoulder as Each Reverse Shoulder is Internally Rotated from 0 to 40° with the Arm at 0° Abduction.

|  | Ant. Deltoid | Mid Deltoid | Post. Deltoid | Subscap | Infraspin | Teres Major | Teres Minor | Pec Major |
|---|---|---|---|---|---|---|---|---|
| 38 mm Equinoxe ®, standard offset | 15.4% | 18.4% | 14.5% | −8.5% | −11.7% | −10.4% | −19.1% | 7.5% |
| 38 mm Equinoxe ®, post/sup offset | 13.5% | 14.9% | 12.5% | −3.1% | −5.4% | −5.0% | −9.3% | 9.8% |

TABLE 7

Average Muscle Length Relative to Normal Shoulder as Each Reverse Shoulder is Externally Rotated from 0 to 40° with the Arm at 0° Abduction.

| | Ant. Deltoid | Mid Deltoid | Post. Deltoid | Subscap | Infraspin | Teres Major | Teres Minor | Pec Major |
|---|---|---|---|---|---|---|---|---|
| 38 mm Equinoxe ®, standard offset | 16.6% | 18.3% | 14.3% | −8.5% | −12.4% | −12.3% | −22.4% | 11.4% |
| 38 mm Equinoxe ®, post/sup offset | 15.6% | 15.0% | 11.3% | −7.1% | −9.0% | −11.9% | −15.2% | 14.4% |

Figures 16A, 16B, 16C:
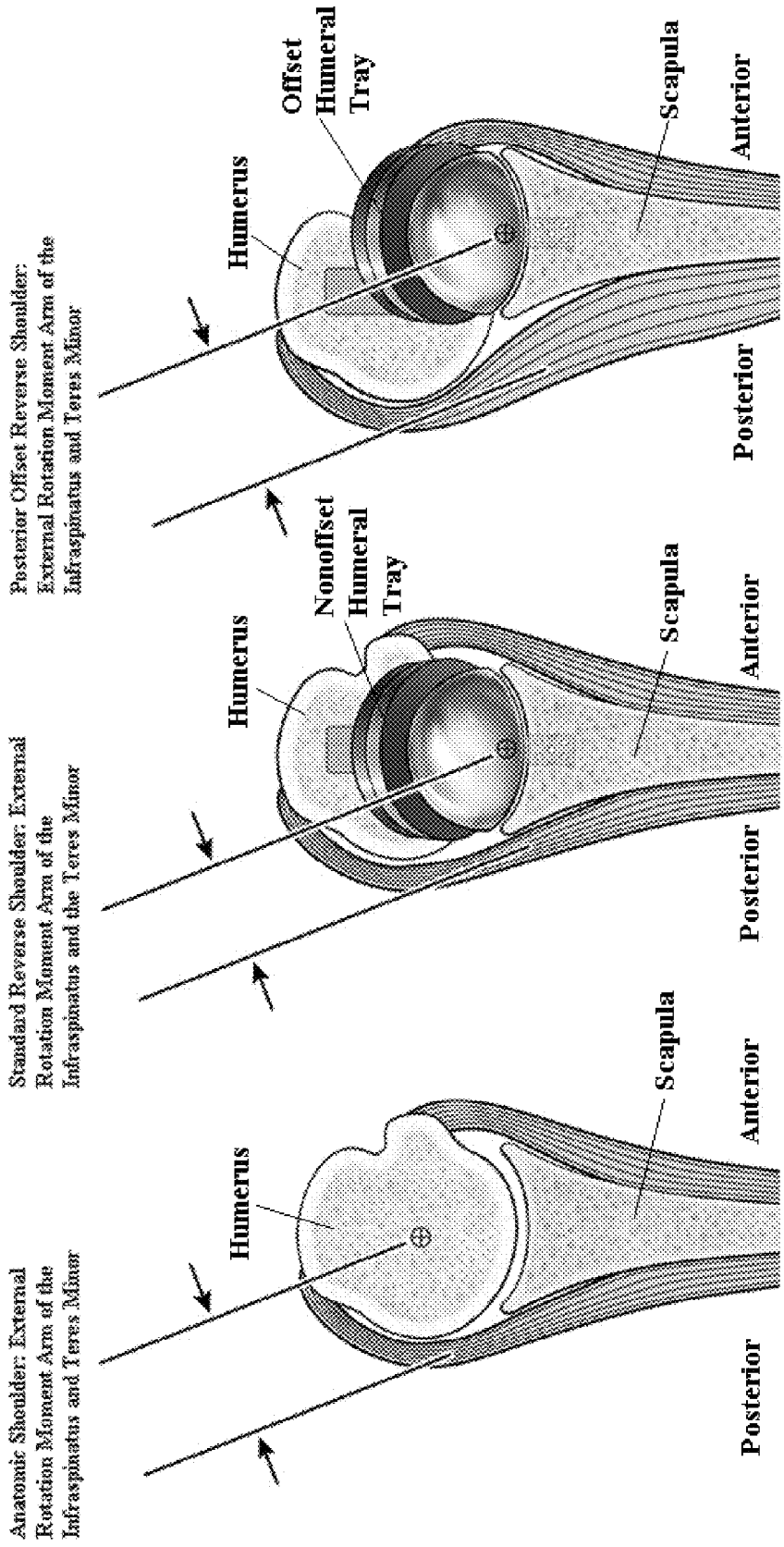
FIGS. 16A, 16B and 16C are images showing how the external rotation moment arms of the posterior rotator cuff muscles (e.g. the infraspinatus and the teres minor) change between an anatomic shoulder, a standard Equinoxe® reverse shoulder assembly (with a non-offset humeral adapter tray), and the reverse shoulder assembly of FIGS. 11A and 11B (with a posterior/superior offset humeral adapter tray). As illustrated, the humeral adapter tray is configured to sit near (above) a resected surface of a humerus.

FIGS. 16A, 16B and 16C are images showing how the external rotation moment arms of the posterior rotator cuff muscles (e.g. the infraspinatus and the teres minor) change between an anatomic shoulder, a standard reverse shoulder, and the posterior/superior offset reverse shoulder of the present invention.

Figure 17C:
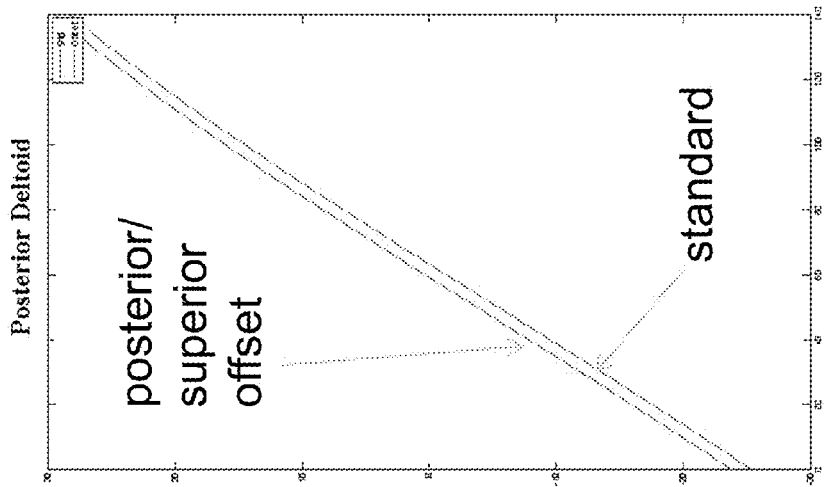
FIGS. 17A, 17B and 17C show a comparison of the standard and posterior/superior offset reverse shoulder moment arms: anterior (FIG. 17A), middle (FIG. 17B), and posterior (FIG. 17C) deltoid abductor moment arms (y-axis) from 0 to 140° abduction in the scapular plane (x-axis).
Figure 17B:
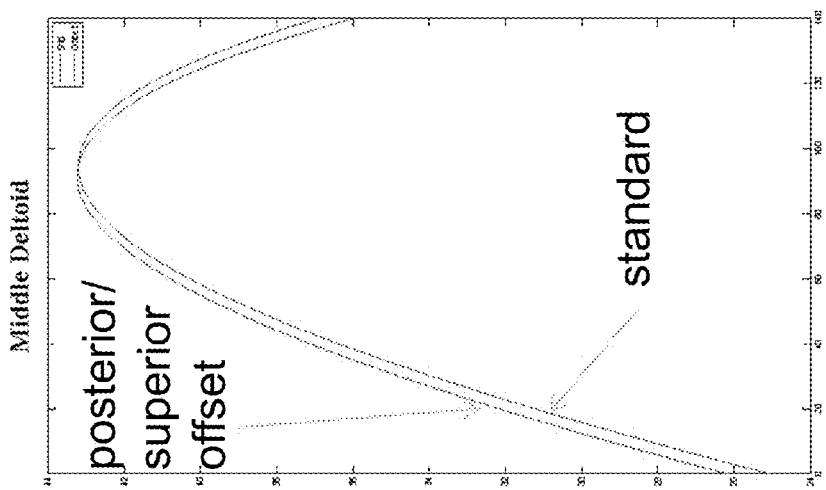
Figure 17A:
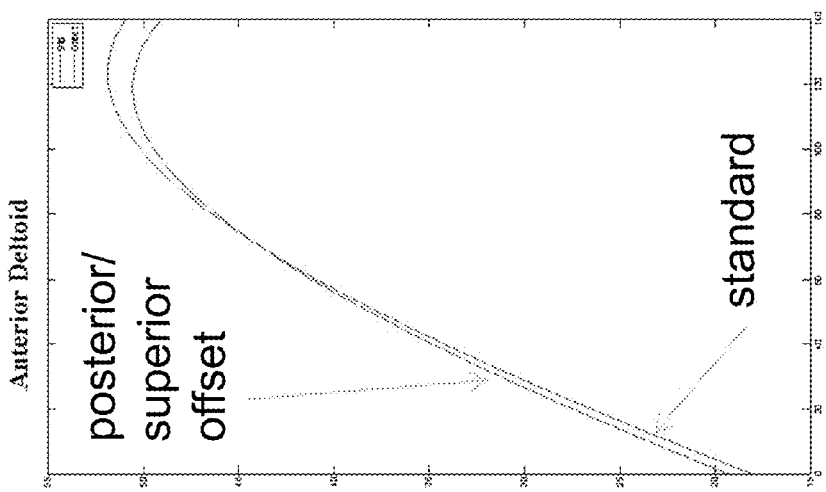
Figures 18A, 18B, 18C:
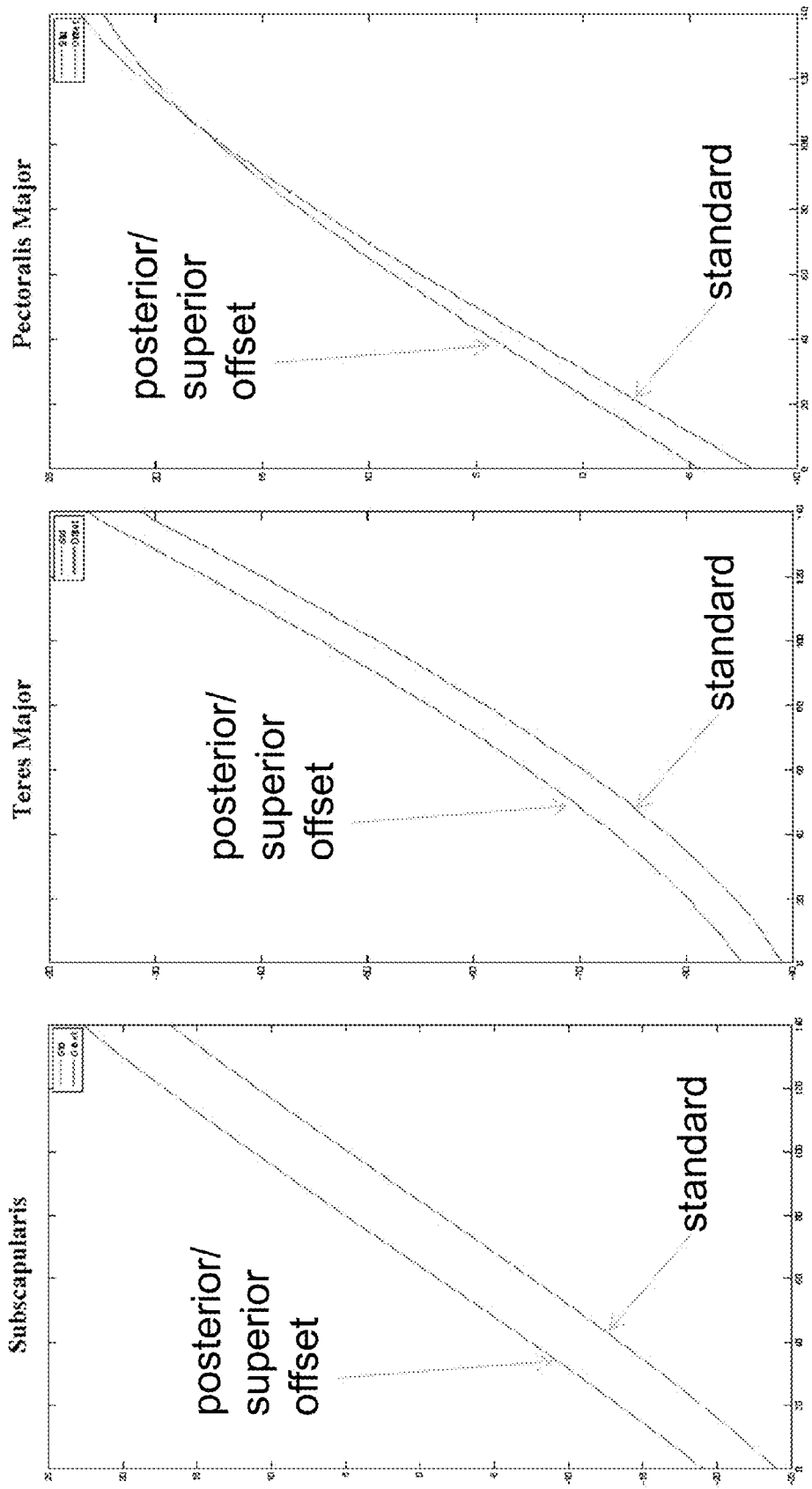
FIGS. 18A, 18B and 18C show a comparison of the standard and posterior/superior offset reverse shoulder moment arms: subscapularis (FIG. 18A), teres major (FIG. 18A), and the pectoralis major (FIG. 18C) abductor moment arms (y-axis) from 0 to 140° abduction in the scapular plane (x-axis).

The abductor moment arms of the 3 heads of the deltoid: anterior (FIG. 17A), middle (FIG. 17B), and posterior (FIG. 17C); the internal rotators: subscapularis (FIG. 18A), teres major (FIG. 18A), and the pectoralis major (FIG. 18C); and the external rotators: infraspinatus (FIG. 19A) and the teres minor (FIG. 19B) during abduction in the scapular plane from 0 to 140° (with scapular motion 1° for every 1.8° of humeral motion) are presented below. As illustrated in FIGS. 17A, 17B and 17C, the standard and posterior/superior offset humeral tray are associated with similar abductor moment arms each of the three heads of the deltoid during abduction in the scapular plane. As illustrated in FIGS. 18A, 18B and 18C, the posterior/superior offset humeral tray is associated with a slightly larger abductor moment arm for the internal rotator muscles: ~5 mm larger for both the subscapularis and the teres major and ~2.5 mm larger for the pectoralis major, relative to the standard (non-offset) humeral tray during abduction in the scapular plane. As illustrated in FIGS. 19A and 19B, the posterior/superior offset humeral tray is associated with a slightly larger abductor moment arm for the external rotator muscles: ~5 mm larger for both the infraspinatus and the teres minor, relative to the standard (non-offset) humeral tray during abduction in the scapular plane. As described in FIGS. 18A-18C and FIGS. 19A-19B, because the posterior/superior offset humeral tray shifts the humerus superiorly relative to the non-offset tray, each anterior/posterior shoulder muscle in FIGS. 18A-18C and FIGS. 19A-19B converts from an adductor to abductor earlier in abduction (e.g. crosses 0 mm), where the subscapularis converts at 62°, the infraspinatus converts at 43°, and the teres minor converts at 110°. For the posterior/superior offset humeral tray to cause each muscle to convert from adductors to abductors earlier potentially results in improved abduction capability by limiting each muscle's antagonistic behavior with the deltoid, thereby, reducing the deltoid force required to elevate the arm.

Figure 20C:
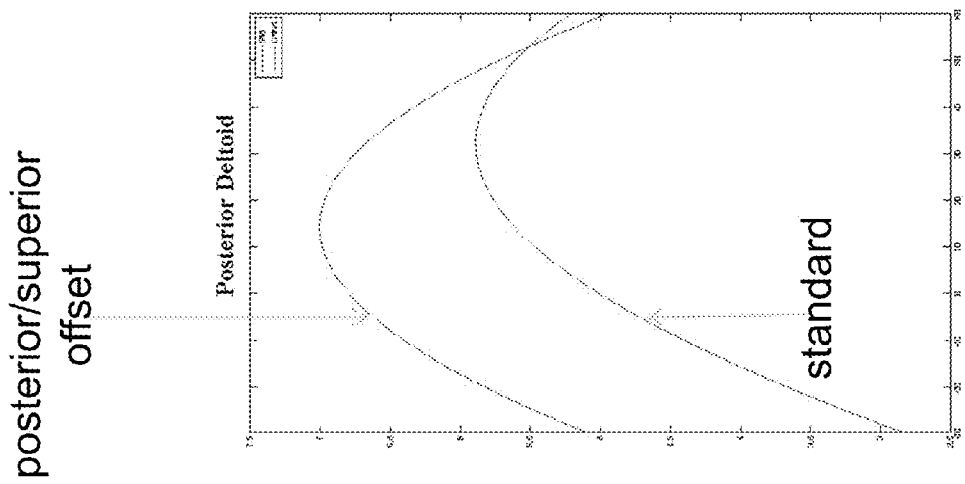
FIGS. 20A, 20B and 20C show a comparison of the standard and posterior/superior offset reverse shoulder moment arms: anterior (FIG. 20A), middle (FIG. 20), and posterior (FIG. 20C) deltoid rotator moment arms (y-axis) from −30 (IR) to 60° (ER) with the arm in 30° abduction (x-axis).
Figure 20B:
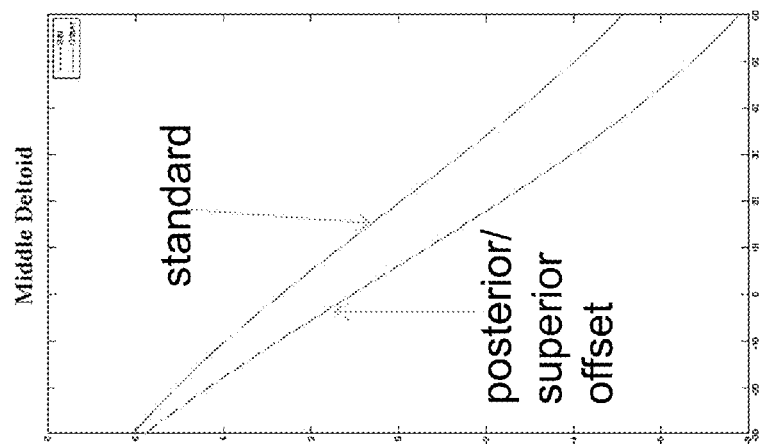
Figure 20A:
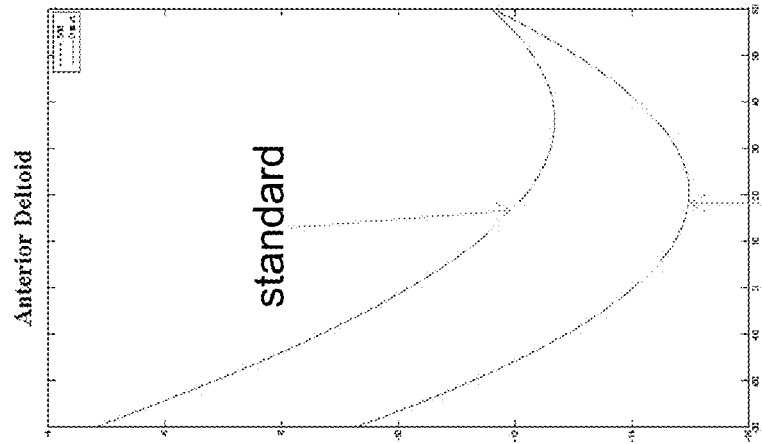
Figures 21A, 21B, 21C:
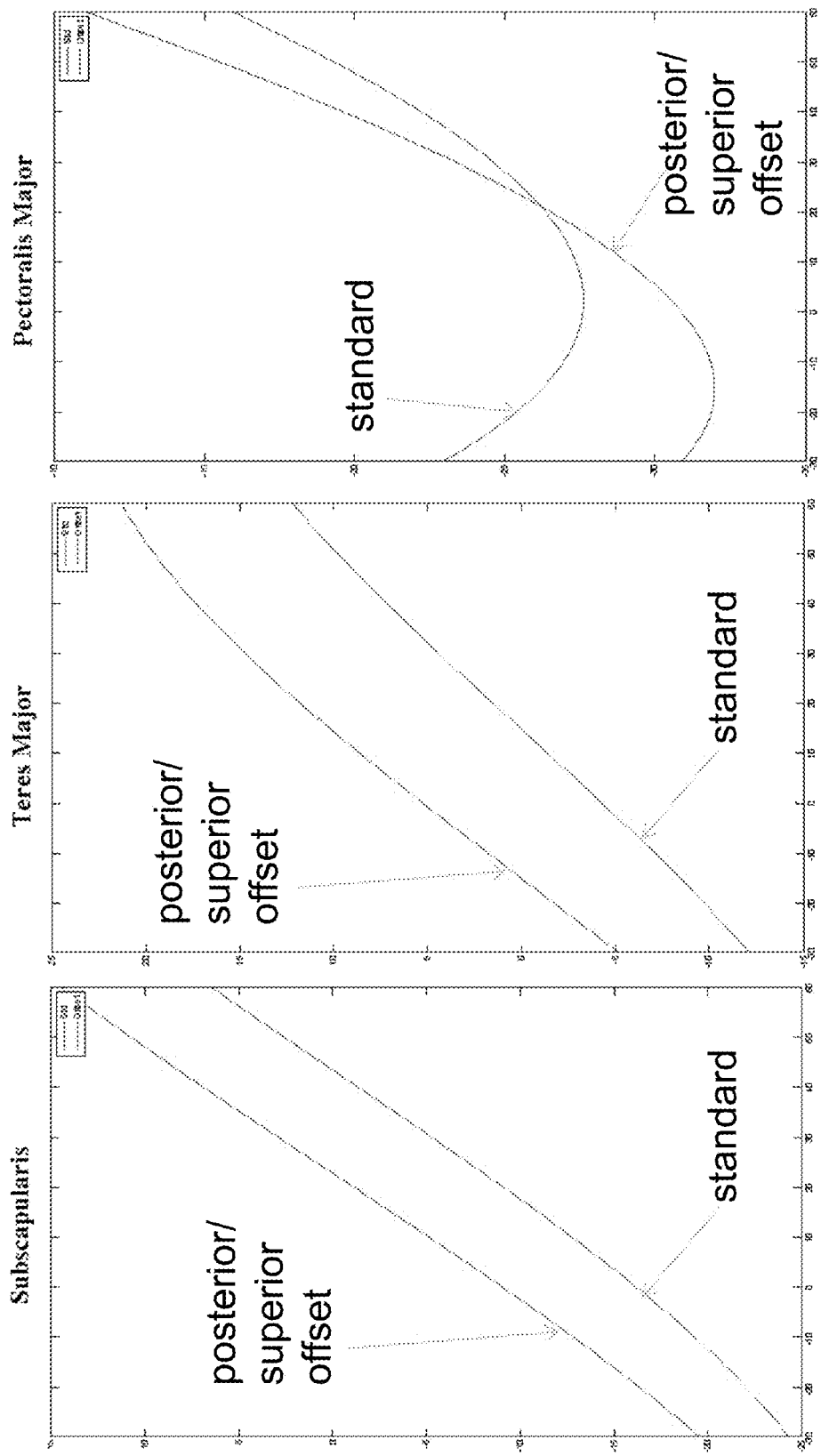
FIGS. 21A, 21B and 21C show a comparison of the standard and posterior/superior offset reverse shoulder moment arms: subscapularis (FIG. 21A), teres major (FIG. 21B), and the pectoralis major (FIG. 21C) rotator moment arms (y-axis) from −30 (IR) to 60° (ER) with the arm in 30° abduction (x-axis).
Figures 22A, 22B:
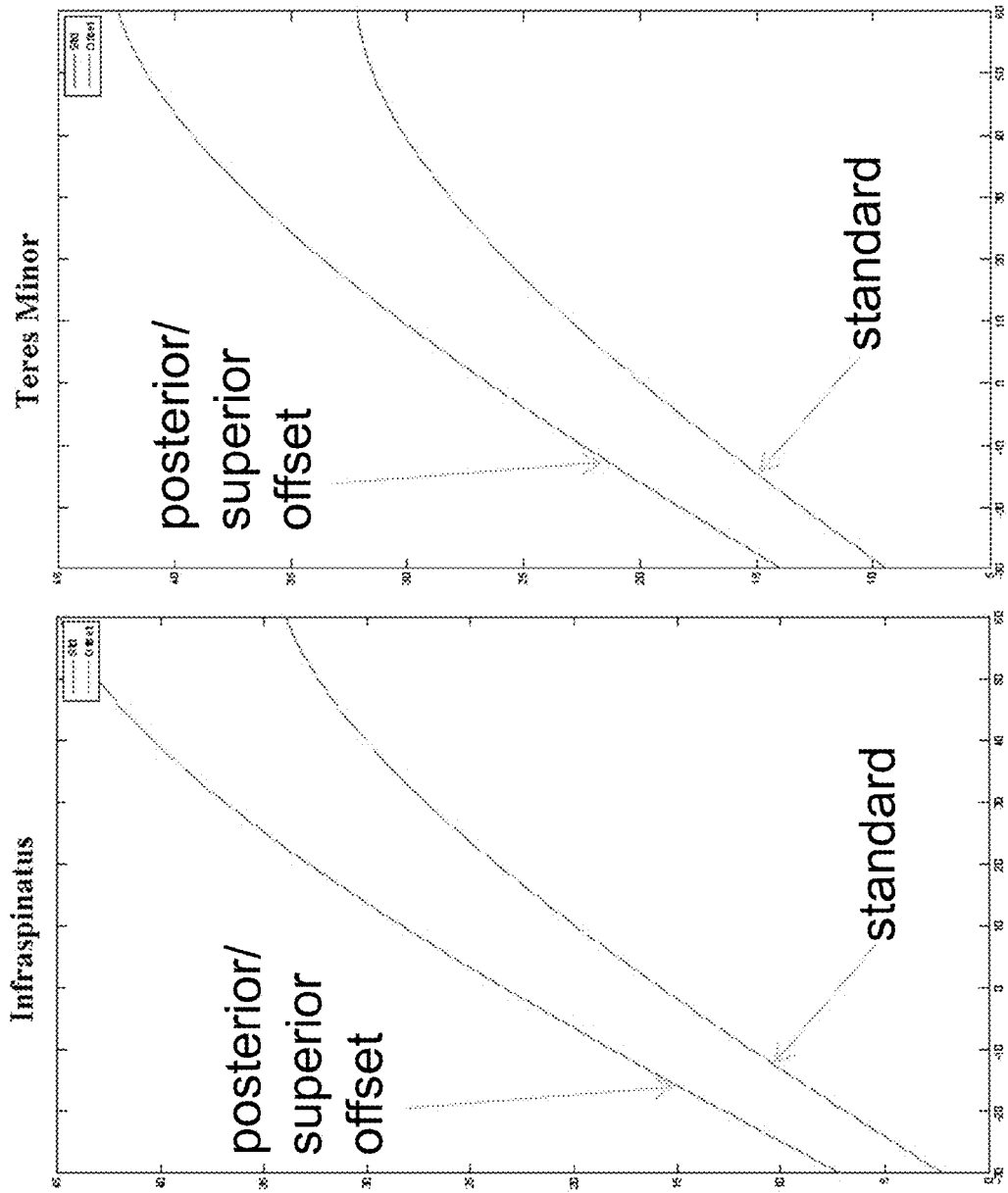
FIGS. 22A and 22B show a comparison of the standard and posterior/superior offset reverse shoulder moment arms infraspinatus (FIG. 22A) and the teres minor (FIG. 22B) rotator moment arms (y-axis) from −30 (IR) to 60° (ER) with the arm in 30° abduction (x-axis).

The internal/external rotator moment arms of the 3 heads of the deltoid: anterior (FIG. 20A), middle (FIG. 20), and posterior (FIG. 20C); the internal rotators: subscapularis (FIG. 18A), teres major (FIG. 18A), and the pectoralis major (FIG. 18C); and the external rotators: infraspinatus (FIG. 19A) and the teres minor (FIG. 19B) during internal rotation from 30 to 0° and external rotation from 0 to 60° with the arm in 30° abduction are presented below. As described in FIGS. 20A-20C, the standard (non-offset) humeral tray is associated with a slightly larger (~4 mm) anterior deltoid rotation moment arm during internal rotation and early into external rotation. Similarly, the standard (non-offset) humeral tray is also associated with a slightly larger (~2 mm) middle deltoid rotation moment arm during internal rotation, relative to the offset humeral tray during IR/ER rotation. Conversely, the posterior/superior offset humeral tray is associated with a slightly larger (~3 mm) posterior deltoid rotation moment arm during internal rotation and early into external rotation, relative to the standard (non-offset) humeral tray during IR/ER rotation. As described in FIGS. 21A-21C, the posterior/superior offset humeral tray is associated with a slightly larger (~5 mm) subscapularis and teres major rotator moment arm during internal and external rotation. Similarly, the posterior/superior offset humeral tray is associated with a slightly larger (~4 mm) pectoralis major rotator moment arm during external rotation, relative to the standard (non-offset) humeral tray during IR/ER rotation. Conversely during internal rotation, the standard (non-offset) humeral tray is associated with a slightly larger (~4 mm) pectoralis major rotator moment arm during internal rotation, relative to the offset humeral tray during IR/ER rotation. As described in FIGS. 22A and 22B, the posterior/superior offset humeral tray 300 is associated with a larger abductor moment arm for the external rotator muscles: ~5 mm larger for both the infraspinatus and the teres minor during internal rotation and ~10 mm larger for both the infraspinatus and the teres minor during external rotation, relative to the standard (non-offset) humeral tray during internal and external rotation. FIGS. 22A and 22B illustrates the moment arms of both the external rotator muscles are substantially increased throughout the range of motion, see Tables 8 and 9. As described in Tables 8 and 9, the posterior/superior offset tray results in a 44% larger external rotation moment arm for the infraspinatus relative to the standard offset humeral tray (28.3 mm vs 19.6 mm)) when the arm is rotated from 30 internal rotation ("IR") to 60 degrees external rotation ("ER"). Similarly, the posterior/superior offset tray results in a 35% larger external rotation moment arm for the teres minor relative to the standard offset humeral tray (30.1 mm vs 22.3 mm) when the arm is rotated from 30 internal rotation to 60 degrees external rotation. Because the posterior/superior offset tray shifts the humerus posteriorly, the internal rotation capability of the subscapularis and teres major is decreased by 7.1 mm and 9.5 mm, respectively, while the external rotation capability of the infraspinatus and teres minor is increased by 8.6 mm and 7.8 mm, respectively. In rotation, the offset humeral tray caused the posterior shoulder muscles to be more effective external rotators. Improved external rotation capability is important for patients with external rotation deficiency; as external rotation is required for many activities of daily living, increasing the rotator moment arm lengths of the only two external rotators is advantageous to restore function.

TABLE 8

Non-offset reverse shoulder rotation moment arms when the humerus is abducted at 30° and rotated from 30° IR to 60° ER

| Non-Offset rTSA | 30° IR | 0° | 30° ER | 60° ER | AVG |
|---|---|---|---|---|---|
| Subscapularis | −24.0 | −16.5 | −5.0 | 6.5 | −9.8 |
| Teres Major | −12.5 | −4.8 | 4.5 | 12.0 | −0.2 |
| Infraspinatus | 2.5 | 15.5 | 26.5 | 34.0 | 19.6 |
| Teres Minor | 9.5 | 19.5 | 28.0 | 32.0 | 22.3 |

TABLE 9

Offset reverse shoulder rotation moment arms (mm) when the humerus is abducted at 30° and rotated from 30° IR to 60° ER

| Offset rTSA | 30° IR | 0° | 30° ER | 60° ER | AVG |
|---|---|---|---|---|---|
| Subscapularis | −19.5 | −9.0 | 4.0 | 14.0 | −2.6 |
| Teres Major | −5.0 | 5.0 | 15.0 | 22.0 | 9.3 |
| Infraspinatus | 7.0 | 24.0 | 37.0 | 45.0 | 28.3 |
| Teres Minor | 14.3 | 26.0 | 37.0 | 43.0 | 30.1 |

Inverting the anatomic concavities with reverse shoulder arthroplasty fundamentally changes the position of the CoR relative to the normal shoulder and causes a shift in the position of the humerus which has implications on deltoid wrapping, muscle tensioning, and muscle moment arms. Offsetting the reverse shoulder humeral adapter tray shifted the humerus in the posterior/superior direction so as to result in better deltoid wrapping, more anatomic muscle tensioning, and larger muscle moment arms during both abduction and internal/external rotation. Specifically, with the posterior/superior offset humeral adapter tray, the middle deltoid wrapping angle was increased, the three heads of the deltoid were able to be over-tensioned less, the pectoralis was tensioned more, and the tension of the subscapularis, infraspinatus, teres major, and teres minor was restored closer to its anatomic tension, relative to the Equinoxe® standard (non-offset) humeral adapter tray. Additionally with the posterior/superior offset humeral adapter tray, the abductor moment arms of the internal and external rotators were increased during abduction and the rotator moment arms of the posterior deltoid, subscapularis, teres major, teres minor, and infraspinatus were increased during internal and external rotation.

While a number of embodiments of the present invention have been described, it is understood that these embodiments are illustrative only, and not restrictive, and that many modifications may become apparent to those of ordinary skill in the art. For example, any element described herein may be provided in any desired size (e.g., any element described herein may be provided in any desired custom size or any element described herein may be provided in any desired size selected from a "family" of sizes, such as small, medium, large). Further, one or more of the components may be made from any of the following materials: (a) any biocompatible material (which biocompatible material may be treated to permit surface bone ingrowth or prohibit surface bone ingrowth—depending upon the desire of the surgeon); (b) a plastic; (c) a fiber; (d) a polymer; (e) a metal (a pure metal such as titanium and/or an alloy such as Ti—Al—Nb, Ti-6Al-4V, stainless steel); (f) any combination thereof. Further still, the metal construct may be a machined metal construct. Further still, the prosthesis may utilize one or more modular elements.

All patents, patent applications, and published references cited herein are hereby incorporated by reference in their entirety. It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A reverse shoulder prosthesis comprising:
   a humeral adapter tray configured to sit near a resected surface of a humerus, the humeral adapter tray comprising:
      a cavity;
      a central bore; and
      a distal face including a boss, the boss:
         (i) configured as an extension of the distal face,
         (ii) posteriorly offset from the central bore by at least 10 mm, and
         (iii) configured to engage a humeral stem; and
   a humeral liner comprising:
      a distal rim configured to sit within the cavity of the humeral adapter tray; and
      a concave articulating surface configured to mate with a convex articulating surface of a glenosphere.

2. The reverse shoulder prosthesis of claim 1 wherein the posteriorly offset boss is configured to posteriorly shift a position of the humerus in order to:
   (i) increase a wrapping angle of a deltoid muscle of a shoulder so as to result in joint stability,
   (ii) tension muscles of a shoulder so as to result in joint stability and improved muscle function, and
   (iii) increase moment arms of internal and external rotators of a shoulder so as to result in improved muscle function.

3. The reverse shoulder prosthesis of claim 1 wherein the humeral adapter tray includes an anti-rotation feature.

4. The reverse shoulder prosthesis of claim 1 wherein the humeral liner includes an anti-rotation feature.

5. The reverse shoulder prosthesis of claim 1 wherein the humeral adapter tray features a dual locking mechanism.

6. The reverse shoulder prosthesis of claim 1 wherein the humeral liner features a dual locking mechanism.

7. The reverse shoulder prosthesis of claim 1 wherein the boss is posteriorly offset from the central bore by a distance ranging from at least 10 mm to 25 mm.

8. The reverse shoulder prosthesis of claim 1 wherein the boss, in addition to being posteriorly offset, is superiorly offset from the central bore by at least 8 mm.

9. The reverse shoulder prosthesis of claim 8 wherein the boss is superiorly offset from the central bore by a distance ranging from at least 8 mm to 25 mm.

10. A reverse shoulder prosthesis comprising:
   a glenoid plate;
   a glenosphere;
   a humeral stem;
   a humeral adapter tray configured to sit near a resected surface of a humerus, the humeral adapter tray comprising:

a cavity;
a central bore; and
a distal face including a boss, the boss:
  (i) configured as an extension of the distal face,
  (ii) posteriorly offset from the central bore by at least 10 mm, and
  (iii) configured to engage a humeral stem; and
a humeral liner comprising:
  a distal rim configured to sit within the cavity of the humeral adapter tray; and
  a concave articulating surface configured to mate with a convex articulating surface of a glenosphere.

11. The reverse shoulder prosthesis of claim 10 wherein the posteriorly offset boss is configured to posteriorly shift a position of the humerus in order to:
  (i) increase a wrapping angle of a deltoid muscle of a shoulder so as to result in joint stability,
  (ii) tension muscles of a shoulder so as to result in joint stability and improved muscle function, and
  (iii) increase moment arms of internal and external rotators of a shoulder so as to result in improved muscle function.

12. The reverse shoulder prosthesis of claim 10 wherein the humeral adapter tray includes an anti-rotation feature.

13. The reverse shoulder prosthesis of claim 10 wherein the humeral liner includes an anti-rotation feature.

14. The reverse shoulder prosthesis of claim 10 wherein the humeral adapter tray features a dual locking mechanism.

15. The reverse shoulder prosthesis of claim 10 wherein the humeral liner features a dual locking mechanism.

16. The reverse shoulder prosthesis of claim 10 wherein the boss is posteriorly offset from the central bore by a distance ranging from at least 10 mm to 25 mm.

17. The reverse shoulder prosthesis of claim 10 wherein the boss, in addition to being posteriorly offset, is superiorly offset from the central bore by at least 8 mm.

18. The reverse shoulder prosthesis of claim 17 wherein the boss is superiorly offset from the central bore by a distance ranging from at least 8 mm to 25 mm.

19. A reverse shoulder prosthesis comprising:
a humeral adapter tray configured to sit near a resected surface of a humerus, the humeral adapter tray comprising:
  a cavity;
  a central bore; and
  a distal face including a boss, the boss:
    (i) configured as an extension of the distal face,
    (ii) superiorly offset from the central bore by at least 8 mm, and
    (iii) configured to engage a humeral stem; and
a humeral liner comprising:
  a distal rim configured to sit within the cavity of the humeral adapter tray; and
  a concave articulating surface configured to mate with a convex articulating surface of a glenosphere.

20. The reverse shoulder prosthesis of claim 19 wherein the boss, in addition to being superiorly offset, is posteriorly offset from the central bore by at least 10 mm.

* * * * *